(12) United States Patent
Zhang et al.

(10) Patent No.: US 10,865,183 B2
(45) Date of Patent: Dec. 15, 2020

(54) COMPOUNDS, REAGENTS, AND USES THEREOF

(71) Applicant: Metabolon, Inc., Morrisville, NC (US)

(72) Inventors: Qibo Zhang, Cary, NC (US); Anne M. Evans, Cary, NC (US)

(73) Assignee: Metabolon, Inc., Morrisville, NC (US)

( * ) Notice: Subject to any disclaimer, the term of this patent is extended or adjusted under 35 U.S.C. 154(b) by 0 days.

(21) Appl. No.: 16/321,135

(22) PCT Filed: Jul. 27, 2017

(86) PCT No.: PCT/US2017/044151
§ 371 (c)(1),
(2) Date: Jan. 28, 2019

(87) PCT Pub. No.: WO2018/022866
PCT Pub. Date: Feb. 1, 2018

(65) Prior Publication Data
US 2019/0152907 A1     May 23, 2019

Related U.S. Application Data

(60) Provisional application No. 62/367,839, filed on Jul. 28, 2016.

(51) Int. Cl.
| | |
|---|---|
| *C07D 207/16* | (2006.01) |
| *A61K 38/00* | (2006.01) |
| *C07K 5/062* | (2006.01) |
| *C07B 59/00* | (2006.01) |
| *G01N 33/53* | (2006.01) |

(52) U.S. Cl.
CPC .......... *C07D 207/16* (2013.01); *C07B 59/002* (2013.01); *C07K 5/06026* (2013.01); *G01N 33/5308* (2013.01); *A61K 38/00* (2013.01); *C07B 2200/05* (2013.01); *G01N 2800/347* (2013.01); *G01N 2800/52* (2013.01)

(58) Field of Classification Search
CPC .............................. C07D 207/16; A61K 38/00
See application file for complete search history.

(56) References Cited

FOREIGN PATENT DOCUMENTS

| | | |
|---|---|---|
| EP | 3081939 A1 | 10/2016 |
| WO | 2014/186311 A1 | 11/2014 |
| WO | 2015/087985 A1 | 6/2015 |

OTHER PUBLICATIONS

Fassett et al., Biomarkers in chronic kidney disease: a review. Kidney Int. Oct. 2011;80(8):806-21.
Gebauer et al., Three-dimensional quantitative structure-activity relationship analyses of peptide substrates of the mammalian H+/peptide cotransporter PEPT1. J Med Chem. Dec. 18, 2003;46(26):5725-34.
Mock et al., Specificity and pH dependence for acylproline cleavage by prolidase. J Biol Chem. Nov. 15, 1990;265(32):19600-5.
International Search Report and Written Opinion for Application No. PCT/US2017/044151, dated Oct. 23, 2017, 12 pages.

*Primary Examiner* — Rebecca L Anderson
(74) *Attorney, Agent, or Firm* — McCarter & English, LLP; Anita M. Bowles; Xin Zhang

(57) ABSTRACT

The present invention provides a compound of formula (I) or a salt thereof and their use as a biomarker in assessing or monitoring kidney function in a subject, determining predisposition to developing reduced kidney function, classifying a subject according to level of kidney function, diagnosing or monitoring chronic kidney disease. Compositions and method of making of the compound of formula (I) are also described.

19 Claims, 21 Drawing Sheets

COMPOUNDS, REAGENTS, AND USES THEREOF

RELATED APPLICATIONS

This application is a 35 U.S.C. § 371 national stage filing of International Application No. PCT/US2017/044151, filed on Jul. 27, 2017, which claims the benefit of the filing date under 35 U.S.C. § 119(e), of U.S. Provisional Application No. 62/367,839, filed on Jul. 28, 2016. The entire contents of each of the foregoing applications, including all drawings, formulae, specifications, and claims, are incorporated herein by reference.

BACKGROUND OF THE INVENTION

There is a significant unmet clinical need for a sensitive, accurate and convenient test to assess the excretory function of the kidneys (glomerular filtration rate, GFR). The most accurate measurement of renal function is the measured glomerular filtration rate (mGFR), which requires the use of ideal filtration markers (e.g., inulin, iothalamate, iohexol). Due to its complexity, this measurement is expensive, difficult to perform in routine clinical practice, and is typically only used in research studies or for potential kidney donors. Consequently, alternative measures of kidney function based on markers such as serum creatinine are used in equations to derive an estimated GFR (eGFR). For example, the MDRDcr, CKD-EPIcr and CKD-EPIcrcys equations currently in use for deriving the eGFR use serum creatinine in combination with demographic information (e.g., age, gender/sex, race). The advantage of this approach is its ease of use in routine clinical practice for the assessment of kidney function. However, these methods of determining the GFR have limitations in truly assessing the kidney function; in some patients some equations under-estimate GFR sometimes and in other patients sometimes over-estimate GFR, especially when it is in the "normal" range. Some of these limitations are likely due to the variability of serum creatinine levels which can be affected by muscle mass, diet, and some drugs, including antibiotics, which leads to variable levels among individuals and over time. The clinical consequence of this inaccuracy leads to the misdiagnosis of patients. In some cases, individuals with chronic kidney disease (CKD) are not diagnosed by current methods and thus they do not receive appropriate treatment (false negative). In other cases, individuals may be diagnosed as having CKD when in fact they do not have CKD (false positive); these individuals are then treated for a disease they do not have. Further, early detection of reduced kidney function due to toxic agents, certain antibiotics, chemotherapy agents, toxicants, toxins), is necessary to detect acute kidney injury (AKI) and take measures to prevent further kidney damage. More recently serum levels of cystatin C have been used to assess kidney function, but the utility of this measure of kidney function is limited by the variability of cystatin C serum levels among individuals. Thus, there is a need for a convenient and more accurate test than the currently available kidney function assessment tests to reduce the number of false negative and false positive diagnoses.

Furthermore, current assessments of kidney function (e.g., serum creatinine, cystatin C eGFR calculations, BUN, urine albumin) are not sufficiently sensitive and/or accurate to detect acute kidney injury (AKI), early kidney disease or to monitor its progression, especially at the earliest stages of AKI and CKD when individuals are asymptomatic. Early detection of declining kidney function could prevent significant deterioration of kidney function that may occur before the problem is detected with currently available methods. A novel test with a sensitive readout that assesses and monitors an individual's kidney function would allow for earlier detection of AKI and/or CKD, before AKI and CKD can be detected with current methods. As a result, the overall cost of treating and managing AKI and CKD and associated complications would be reduced. With early detection of CKD, complications, including cardiovascular disease, anemia, malnutrition and bone disease, can be more effectively treated or possibly even prevented. Early detection of CKD would enable lifestyle modifications such as healthy diet, smoking cessation, weight loss, and treatment of high blood pressure, which could prevent or reduce further kidney injury, thereby reducing the need for dialysis and kidney transplant which are frequent outcomes associated with reduced kidney function and CKD.

Therefore, there is an unmet need for a blood- or urine-based test that can assess and/or monitor a patient's renal function by measuring the level of one or more biomarker metabolites in asymptomatic patients, in patients with risk factors for CKD or AKI (e.g., age over 60, hypertension, diabetes, cardiovascular disease, family history of CKD), and in patients in response to a composition or therapeutic intervention. For example, the test can quantitatively measure the level of a panel of biomarker metabolites whereby the increase or decrease in the level of each biomarker in the panel relative to a standard reference level are indicative of kidney function. Such biomarker test panels could replace or supplement current kidney function test results and enable physicians to better assess kidney function initially and/or to monitor kidney function in patients over time. Such a test could also be useful in assessing the effect of therapeutic interventions to slow kidney function decline.

SUMMARY OF THE INVENTION

The present invention provides novel compounds and compositions and their use in assessing and monitoring kidney function as well as diagnostic methods for kidney diseases.

In one embodiment, the present invention provides a compound represented by formula (I):

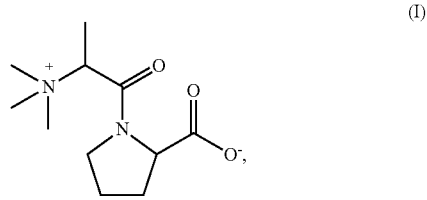

or a salt thereof, wherein the compound is at least 60%, 70%, 80%, 90%, 95%, 99%, 99.5% or 99.9% pure.

In another embodiment, the present invention provides a method for determining the level of a compound of formula (I) or salt thereof, in a subject comprising: (1) preparing an analytical sample from a biological sample obtained from the subject; and (2) determining the level of the compound using chromatography, mass spectrometry, enzyme-linked immunosorbent assay (ELISA), antibody linkage, immunoblotting, immunohistochemistry (IHC), other immunochemical methods, or a combination thereof.

In another embodiment, the present invention provides a method for assessing kidney function in a subject comprising: determining the level of a compound represented by formula (I) or a salt thereof, in a biological sample obtained from the subject, using chromatography, mass spectrometry, enzyme-linked immunosorbent assay (ELISA), antibody linkage, immunoblotting, immunohistochemistry (IHC), other immunochemical methods, or a combination thereof, wherein an elevated level of the compound in the biological sample as compared to a reference level is indicative of reduced kidney function in the subject.

In another embodiment, the present invention provides a method for determining predisposition to developing reduced kidney function in a subject comprising: determining the level of a compound represented by formula (I) or a salt thereof, in a biological sample obtained from the subject, using chromatography, mass spectrometry, enzyme-linked immunosorbent assay (ELISA), antibody linkage, immunoblotting, immunohistochemistry (IHC), other immunochemical methods, or a combination thereof, wherein an elevated level of the compound in the biological sample as compared to a reference level is indicative of predisposition to developing reduced kidney function in the subject.

In yet another embodiment, the present invention provides a method for classifying (or staging) a subject according to level (or stage) of kidney function comprising: determining the level of a compound represented by formula (I) or a salt thereof, in a biological sample obtained from the subject, using chromatography, mass spectrometry, enzyme-linked immunosorbent assay (ELISA), antibody linkage, immunoblotting, immunohistochemistry (IHC), other immunochemical methods, or a combination thereof, wherein the level of the compound in the biological sample as compared to a reference level is used in classifying the subject according to level of kidney function.

In yet another embodiment, the present invention provides a method for monitoring kidney function in a subject comprising:

(1) determining the level of a compound represented by formula (I) or a salt thereof, in a first biological sample obtained from the subject at a first time point; and (2) determining the level of the compound or a salt thereof in a second biological sample obtained from the subject at a second time, wherein the second time is later than the first time, and wherein the level of the compound is determined using chromatography, mass spectrometry, enzyme-linked immunosorbent assay (ELISA), antibody linkage, immunoblotting, immunohistochemistry (IHC), other immunochemical methods, or a combination thereof;

wherein a change in the level of the compound in the second biological sample from the level in the first biological sample is indicative of a change in kidney function.

In yet another embodiment, the present invention provides a method for diagnosing chronic kidney disease (CKD) in a subject comprising: determining the level of a compound represented by formula (I) or a salt thereof, in a biological sample obtained from the subject, using chromatography, mass spectrometry, enzyme-linked immunosorbent assay (ELISA), antibody linkage, immunoblotting, immunohistochemistry (IHC), other immunochemical methods, or a combination thereof, wherein an elevated level of the compound in the biological sample as compared to a reference level is indicative of chronic kidney disease.

In another embodiment, the present invention provides a method for monitoring the progression or regression of chronic kidney disease (CKD) in a subject comprising:

(1) determining the level of a compound represented by formula (I) or a salt thereof, in a first biological sample obtained from the subject at a first time point;

(2) determining the level of the compound or a salt thereof in a second biological sample obtained from the subject at a second time, wherein the second time is later than the first time, wherein a change in the level of the compound in the second biological sample from the level in the first biological sample is indicative of progression or regression of the disease in the subject and wherein the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In yet another embodiment, the present invention provides a method for diagnosing acute kidney injury (AKI) in a subject comprising: determining the level of a compound represented by formula (I) or a salt thereof, in a biological sample obtained from the subject, using chromatography, mass spectrometry, enzyme-linked immunosorbent assay (ELIS A), antibody linkage, immunoblotting, immunohistochemistry (IHC), other immunochemical methods, or a combination thereof, wherein an elevated level of the compound in the biological sample as compared to a reference level is indicative of chronic kidney disease.

In another embodiment, the present invention provides a method for monitoring the progression or regression of acute kidney injury (AKI) in a subject comprising:

(1) determining the level of a compound represented by formula (I) or a salt thereof, in a first biological sample obtained from the subject at a first time point;

(2) determining the level of the compound or a salt thereof in a second biological sample obtained from the subject at a second time, wherein the second time is later than the first time, wherein a change in the level of the compound in the second biological sample from the level in the first biological sample is indicative of progression or regression of the disease in the subject and wherein the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

In yet another embodiment, the present invention provides a method of assessing kidney function in a subject in response to a composition comprising: determining the level of a compound represented by formula (I) or a salt thereof, in a biological sample obtained from a subject treated with the composition, using chromatography, mass spectrometry, enzyme-linked immunosorbent assay (ELISA), antibody linkage, immunoblotting, immunohistochemistry (IHC), other immunochemical methods, or a combination thereof, wherein an elevated level of the compound in the biological sample as compared to the level of the compound in the subject without the treatment with the composition is indicative of reduced kidney function (and may indicate AKI).

In another embodiment, the present invention provides a method for treating a subject having chronic kidney disease (CKD) comprising:

(1) determining the level of a compound represented by formula (I) or a salt thereof, in a biological sample obtained from the subject using chromatography, mass spectrometry, enzyme-linked immunosorbent assay (ELISA), antibody linkage, immunoblotting, immunohistochemistry (IHC), other immunochemical methods, or a combination thereof;

(2) administering to the subject an effective therapy suitable for treating chronic kidney disease if the subject has an elevated level of the compound as compared to a reference level.

In another embodiment, the present invention provides a method for treating a subject having chronic kidney disease (CKD) comprising administering to the subject an effective therapy suitable for treating chronic kidney disease, wherein the subject has an elevated level of a compound represented by formula (I) or a salt thereof, as compared to a reference level.

In yet another embodiment, the present invention provides a method for treating a subject having acute kidney injury (AKI) comprising administering to the subject an effective therapy suitable for treating AKI, wherein the subject has an elevated level of a compound represented by formula (I) or a salt thereof, as compared to a reference level.

In another embodiment, the present invention provides method for treating a subject having AKI comprising:

(1) determining the level of a compound represented by formula (I) or a salt thereof, in a biological sample obtained from the subject using chromatography, mass spectrometry, enzyme-linked immunosorbent assay (ELISA), antibody linkage, immunoblotting, immunohistochemistry (IHC), other immunochemical methods, or a combination thereof;

(2) administering to the subject an effective therapy suitable for treating AKI if the subject has an elevated level of the compound as compared to a reference level.

In some instances the AKI may be due to treatment (e.g., chemotherapy, treatment with a therapeutic agent). In such instances the therapeutic intervention would be to discontinue the chemotherapy or drug treatment or use a substitute or alternative drug for treatment.

In yet another embodiment, the present invention provides a method for treating a subject having acute kidney injury (AKI) comprising administering to the subject an effective therapy suitable for treating AKI, wherein the subject has an elevated level of a compound represented by formula (I) or a salt thereof, as compared to a reference level.

In another embodiment, the present invention provides a method for calculating the estimated glomerular filtration rate (eGFR) in a subject comprising the steps of:

1) determining the level of a compound represented by formula (I) or a salt thereof, in a biological sample obtained from the subject, using chromatography, mass spectrometry, enzyme-linked immunosorbent assay (ELISA), antibody linkage, immunoblotting, immunohistochemistry (IHC), other immunochemical methods, or a combination thereof; and 2) calculating the eGFR using an algorithm that utilizes the determined level of the compound.

The present invention also provides kits comprising a compound of formula (I) or a salt thereof.

In another embodiment, the kit of the present invention comprises a compound of formula (I) or a salt thereof and instructions for measuring the level of the compound of formula (I) in a biological sample.

In another embodiment, the kit includes an internal standard comprising a labeled compound of formula (I) or a salt thereof and instructions for measuring the level of the compound of formula (I) or a salt thereof in a biological sample.

In yet another embodiment, the kit includes a compound of formula (I) or a salt thereof, a labeled compound of formula (I) or a salt thereof, and instructions for measuring the level of the compound of formula (I) in a biological sample.

In one embodiment, the kit of the present invention comprises a compound of formula (I) or a salt thereof and instructions for assessing or monitoring kidney function in a subject based on the level of the compound detected in a biological sample obtained from the subject.

In another embodiment, the kit of the present invention comprises a compound of formula (I) or a salt thereof and instructions for determining predisposition to developing reduced kidney function in a subject based on the level of the compound detected in a biological sample obtained from the subject.

In another embodiment, the kit of the present invention comprises a compound of formula (I) or a salt thereof and instructions for classifying a subject according to level of kidney function based on the level of the compound detected in a biological sample obtained from the subject.

In yet another embodiment, the kit of the present invention comprises a compound of formula (I) or a salt thereof and instructions for diagnosing or monitoring chronic kidney disease (CKD) in a subject based on the level of the compound detected in a biological sample obtained from the subject.

In yet another embodiment, the kit of the present invention comprises a compound of formula (I) or a salt thereof and instructions for diagnosing or monitoring acute kidney injury (AKI) in a subject based on the level of the compound detected in a biological sample obtained from the subject.

In another embodiment, the kit of the present invention comprises a compound of formula (I) or a salt thereof and instructions for calculating the estimated glomerular filtration rate (eGFR) in a subject based on the level of the compound detected in a biological sample obtained from the subject.

DETAILED DESCRIPTION OF THE INVENTION

Definitions

Figure 1:
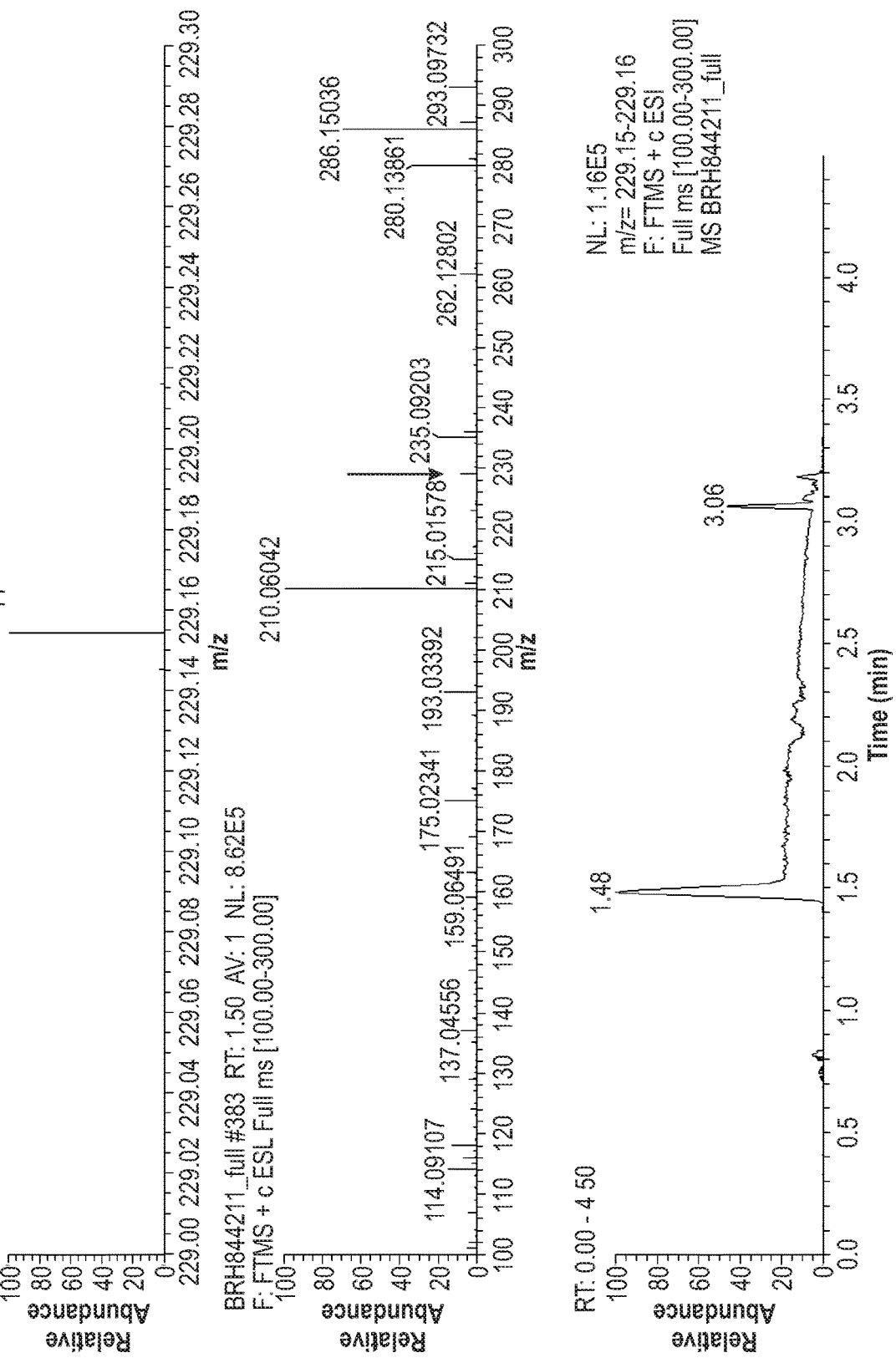
FIG. 1 shows LC/MS chromatogram and spectrum of compound A in human plasma sample.

Unless otherwise specified, the below terms used herein are defined as follows:

The compounds of the invention may be present in the form of salts. Any suitable organic or inorganic salts are included in the present invention. In certain embodiments, the salts of the compounds of the invention refer to non-toxic "pharmaceutically acceptable salts." The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Pharmaceutically acceptable salt forms include pharmaceutically acceptable acidic/anionic or basic/cationic salts. Examples of pharmaceutically acceptable salts include, but are not limited to, mineral or organic acid salts of basic residues such as amines; alkali or organic salts of acidic residues such as carboxylic acids; and the like.

For example, such salts include, the acetate, ascorbate, benzenesulfonate, benzoate, bezylate, bicarbonate, bitartrate, bromide, calcium edetate, camsylate, carbonate, chloride, citrate, dihydrochloride, edetate, edisylate, ethane disulfonate, estolate, esylate, fumarate, glyceptate, gluconate, glutamate, glycolate, glycollylarsanilate, hexylresorcinate, hydrabamine, hydrobromide, hydrochloride, hydroxymaleate, hydroxynaphthoate, iodide, isethionate, lactate, lactobionate, malate, maleate, mandelate, methanesulfonate, mesylate, methylbromide, methylnitrate, methylsulfate, mucate, napsylate, nitrate, oxalate, pamoate, pantothenate, phenylacetate, phosphate/diphosphate, polygalacturonate, propionate, salicylate, stearate, subacetate, succinate, sulfamide, sulfate, tannate, tartrate, teoclate, tosylate, triethiodide, ammonium, benzathine, chloroprocaine, colline, diethanolamine, ethylenediamine, meglumine and procaine salts. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which, for example, are useful for purifying or isolating the compounds of the present invention (e.g. trifluoroacetate salts) also comprise a part of the invention.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 95%, 99% or 99.9% by weight pure relative to the other stereoisomers. When a single enantiomer is named or depicted by structure, the depicted or named enantiomer is at least 60%, 70%, 80%, 90%, 95%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

When compounds having one or more stereocenters are depicted with particular stereochemistry for at least one stereocenter, the present invention also includes compounds that have the opposite stereochemistry at the corresponding stereocenter(s) and compounds that have no specific stereochemistry at the corresponding stereocenter(s).

"Treating" a condition or disease refers to curing as well as ameliorating at least one symptom of the condition or disease.

As used herein, the term "subject" means any animal, but is preferably a mammal, such as, for example, a human, monkey, non-human primate, rat, mouse, cow, dog, cat, pig, horse, or rabbit. Even more preferably, the subject is a human.

As used herein, "effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day or from about 0.1 mg/kg/day to about 100 mg/kg/day.

"Diabetes," as used herein, refers to a group of metabolic diseases characterized by high blood sugar (glucose) levels which result from defects in insulin secretion or action, or both.

"Type 2 diabetes," as used herein refers to one of the two major types of diabetes, the type in which the beta cells of the pancreas produce insulin, at least in the early stages of the disease, but the body is unable to use it effectively because the cells of the body are resistant to the action of insulin. In later stages of the disease the beta cells may stop producing insulin. Type 2 diabetes is also known as insulin-resistant diabetes, non-insulin dependent diabetes and adult-onset diabetes.

As used herein, the term "biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). Alternatively, the biomarkers demonstrate a correlation with kidney function. The range of possible correlations is between negative (−)1 and positive (+)1. A result of negative (−)1 means a perfect negative correlation and a positive (+)1 means a perfect positive correlation, and 0 means no correlation at all. A "substantial positive correlation" refers to a biomarker having a correlation from +0.25 to +1.0 with a disorder or with a clinical measurement (e.g., mGFR), while a "substantial negative correlation" refers to a correlation from −0.25 to −1.0 with a given disorder or clinical measurement. A "significant positive correlation" refers to a biomarker having a correlation of from +0.5 to +1.0 with a given disorder or clinical measurement (e.g., mGFR), while a "significant negative correlation" refers to a correlation to a disorder of from −0.5 to −1.0 with a given disorder or clinical measurement.

The "level" of the compound of the present invention or one or more additional biomarkers means the absolute or relative amount or concentration of the biomarker measured in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, kidney tissue, blood, blood plasma (plasma), blood serum (serum), urine, saliva, or cerebral spinal fluid (CSF). Preferably, the biological sample is blood, blood plasma, serum, saliva or urine. In another preferred embodiment, the biological sample is blood serum or blood plasma.

A "reference level" means a level of the compound of the present invention or additional biomarker(s) that is indicative of a particular disease state, phenotype, or lack thereof, as well as combinations of disease states, phenotypes, or lack thereof. A "reference level" may be an absolute or relative amount or concentration of the compound of the present invention or additional biomarker(s), a presence or absence of the compound of the present invention or additional biomarker(s), a range of amount or concentration of the compound of the present invention or additional biomarker(s), a minimum and/or maximum amount or concentration of the compound of the present invention or additional biomarker(s), a mean amount or concentration of the compound of the present invention or additional biomarker(s), and/or a median amount or concentration of the compound of the present invention or additional biomarker(s); and, in addition, "reference levels" of combinations of the compound of the present invention and additional biomarker(s) may also be ratios of absolute or relative amounts or concentrations of two or more biomarkers with respect to each other. Appropriate reference levels of the compound of the present invention or additional biomarker(s) for a particular disease state, phenotype, or lack thereof may be determined by measuring levels of the compound of the present invention or desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). A "positive" reference level means a level that is indicative of a particular disease state or phenotype. A "negative" reference level means a level that is indicative of a lack of a particular disease state or phenotype. For example, a "CKD-positive reference level" means a level of the compound of the present invention or additional biomarker that is indicative of a positive diagnosis of CKD in a subject, and a "CKD-negative reference level" means a level of the compound of the present invention or additional biomarker that is indicative of a negative diagnosis of CKD in a subject (i.e., normal kidney function, absence of CKD). Likewise, a "kidney function reference level" may indicate the degree of kidney function present in a subject. For example, a "normal kidney function reference level" means a level of the compound of the present invention or additional biomarker that is indicative of normal kidney function in a subject, a "moderately reduced kidney function reference level" means a level of the compound of the present invention or additional biomarker that is indicative of moderately reduced kidney function, and a "severely reduced kidney function reference level" means a level of the compound of the present invention or additional biomarker that is indicative of severely reduced kidney function in a subject As used herein, a "reference sample" refers to a sample containing reference level of a biomarker. For example, a reference sample can be obtained from a subject that does not have a particular disease, disease state or phenotype, such as CKD or acute kidney injury.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

As used herein, the term "metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Glomerular filtration rate" or "GFR" is the volume of fluid filtered from the renal glomerular capillaries into the Bowman's capsule per unit time. The GFR is a metric of kidney function whereby GFR at or above a certain threshold indicates normal kidney function and GFR below the threshold value indicates kidney function is compromised or impaired. Generally, a high GFR value indicates better kidney function while a low GFR indicates kidney function impairment (e.g., chronic kidney disease, acute kidney injury).

"Measured glomerular filtration rate" or "mGFR" means the actual glomerular filtration rate which is determined using a filtration marker such as inulin, iothalamate or iohexol. mGFR is performed in a clinical setting and is the most accurate measurement of renal function.

"Estimated glomerular filtration rate" or "eGFR" means a calculated estimate of the actual glomerular filtration rate. The calculated value may be based on the level of one or more biomarkers and may include other variables such as demographic information (e.g., age or gender). One current method for calculating eGFR is based on serum creatinine concentration. Other current methods for calculating an eGFR use the amount of cystatin C alone or in combination with the amount of serum creatinine. Generally, low eGFR values are associated with decreased kidney function.

"SrCr eGFR" or "eGFRscr, eGFRcr" means the eGFR estimation based on serum creatinine levels.

"CKD-EPI" or "Chronic Kidney Disease Epidemiology Collaboration" derived two equations for calculating an eGFR. One equation is: CKD-EPIcr GFR=141× min(SCr/κ,1)$^α$X max(SCr/κ,1)$^{-1/209}$×0.993$^{Age}$×1.018 [if female]×1.159 [if black], where SCr is serum creatinine (mg/dL), κ is 0.7 for females and 0.9 for males, α is −0.329 for females and −0.411 for males, min indicates the minimum of SCr/κ or 1, and max indicates the maximum of SCr/κ or 1. The second equation (CKD-EPIcycys eGFR) includes the amount of Cystatin C in addition to the SCr amount and demographic variables.

"MDRD or "Modification of Diet in Renal Disease eGFR" is another equation for calculating an eGFR. The equation is: MDRDcr eGFR=186× (SCr)$^{-1.154}$× (Age)$^{-0.203}$× (0.742 if female)×(1.212 if Black), where SCr is serum creatinine (mg/dL). Currently, the MDRDcr eGFR is typically regarded as the standard of care method to calculate the eGFR.

"Urine albumin" is a test measuring the amount of albumin in the urine and is also used to detect kidney disease.

"Serum creatinine" or "SCr" refers to the measurement of creatinine in serum and is commonly used to estimate GFR.

"Blood urea nitrogen" or "BUN" refers to the measurement of the amount of nitrogen in the blood in the form of urea. BUN is a test used to measure kidney function.

"Chronic Kidney Disease" or "CKD" includes conditions that damage kidneys resulting in decreased ability of the kidney to remove wastes from the body resulting in high levels of the wastes in the body and leading to increased risk of illness and development of complications such as high blood pressure, anemia, poor nutritional health and nerve damage. Patients with abnormalities in kidney function for at least three months may be diagnosed with CKD. Kidney damage due to CKD is permanent.

"Acute kidney injury" or "AKI" refers to a condition in which there is a rapid loss of kidney function. Kidney damage due to AKI may be reversible.

"Chronic Kidney Disease Stages" or "CKD Stages" means the degree of kidney damage as currently assessed using the measured or estimated glomerular filtration rate (mGFR, eGFR). Clinically, 5 stages of CKD are generally recognized with kidney function regarded as normal in Stage 1 (GFR>90), minimally reduced in Stage 2 (GFR 60-89), moderately reduced in Stages 3 A and 3B (GFR 30-59), severely reduced in Stage 4 (GFR 15-29) and very severe or endstage kidney failure, also referred to as established renal failure at Stage 5 (GFR <15, or on dialysis). Kidney function stages may be used to refer to kidney damage present for any amount of time (i.e., kidney damage due to AKI or CKD).

The present invention can be understood more fully by reference to the following detailed description and examples, which are intended to exemplify non-limiting embodiments of the invention.

Compounds and Compositions

The present invention provides novel compounds, compositions and their use in diagnostic methods and treatment methods.

In a 1st embodiment, the present invention provides a compound represented by the following formula:

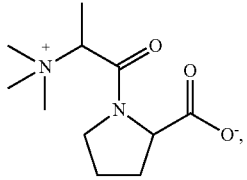

(I)

or a salt thereof.

In certain embodiments, the compound of formula (I) in the 1st embodiment is represented by the following formula:

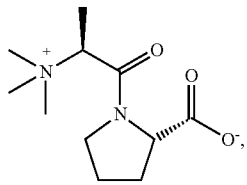

(II)

or a salt thereof.

In one embodiment, the compound of formula (II) or a salt thereof is at least 60% optically pure, at least 70% optically pure, at least 80% optically pure, at least 90% optically pure, at least 95% optically pure, or at least 99% optically pure.

In various embodiments, the compound of the present invention described herein (e.g., compounds represented by formula (I) or (II) or a salt thereof) is substantially free of impurities.

In various embodiments, the compound of the present invention described herein (e.g., compounds represented by formula (I) or (II), or a salt thereof) is at least 60% pure, at least 70% pure, at least 80% pure, at least 90% pure, at least 95% pure or at least 99% pure.

In certain embodiments, the compound of the present invention described herein (e.g., compounds represented by formula (I) or (II) or a salt thereof) is isotopically labeled. In one embodiment, the compound of formula (I) or (II) or a salt thereof is radiolabeled, such as with tritium ($^{3}$H) or carbon 14 ($^{14}$C). In another embodiment, the compound of formula (I) or (II) or a salt thereof is labeled with deuterium, carbon 13 ($^{13}$C), or nitrogen 15 ($^{15}$N), or a combination thereof. Any suitable methods for isotopic labeling of the compounds of the present invention can be used.

As used herein, when a compound of the present invention (e.g., compounds represented by formula (I) or (II) or a salt thereof) is isotopically labeled, it means that the position that carries the isotopic label has the designated isotope at an abundance that is at least 10 times, 50 times, 100 times, or 1000 times higher than the natural abundance. For example, when a compound of the present invention (e.g., compounds represented by formula (I) or (II) or a salt thereof) is labeled with carbon 13 ($^{13}$C), the position that carries the $^{13}$C label has at least 10%, 20%, 30%, 40%, 50%, 60%, 70%, 80%, 90%, 95%, 99% $^{13}$C incorporation at that position. Similarly, when a compound of the present invention (e.g., compounds represented by formula (I) or (II) or a salt thereof) is labeled with deuterium, the position that carries the deuterium has at least 10%, 20%, 30%, 40%, 50%, 60%, 70%, 80%, 90%, 95%, 99% deuterium incorporation at the position.

The compounds described above, such as compounds of formulas (I) or (II) or a salt (e.g., a pharmaceutically acceptable salt) thereof, can be used in any of the methods described herein. For example, the compounds of the present invention can be used to assess kidney function in a subject, to calculate an estimate of the glomerular filtration rate in a subject, to monitor a subject to detect changes in kidney function (e.g., decreases in function which may indicate acute kidney injury or incipient CKD), to classify subjects according to the degree of kidney function (e.g., normal, mildly reduced, moderately reduced, severely reduced, end-stage kidney failure) and to distinguish subjects having CKD vs. control subjects not diagnosed with CKD. Further, the compounds may be used to monitor changes in kidney function over time or in response to drug treatment, disease (e.g., type II diabetes), or lifestyle interventions (e.g., diet, exercise) and to identify or rule-out subjects as suitable candidates for drug therapies and/or kidney transplant.

Also included in the present invention are antibodies or antibody fragments that specifically bind to the compound described herein (e.g. compound of formula (I) or (II) or a salt (e.g., a pharmaceutically acceptable salt) thereof). Methods for generating antibodies that specifically binds to small molecules are known in the art. Antibody derivatives, such as a polypeptide comprising the $V_H$ and $V_L$ sequences of the antibody described above are also included. In certain embodiment, the polypeptide is a fusion protein. The present invention also includes cells for producing the antibodies or antibody fragments and the antibody derivatives described herein. In one embodiment, the cell is an eukaryotic cell.

Methods

In a 2nd embodiment, the present invention provides a method for determining the level of the compound of the present invention (e.g., compound of formula (I) or (II) or a salt thereof), in a subject comprising: (1) obtaining a biological sample from the subject; and (2) determining the level of the compound.

Any suitable method may be used to analyze the biological sample in order to determine the level of the compound of the present invention (e.g., compound of formula (I) or (II) or a salt thereof) in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, immunoblotting, immunohistochemistry (IHC), other immunochemical techniques, and combinations thereof.

In one example, the biological sample may be subjected to liquid chromatography (LC) prior to mass spectrometry. LC methods may include, for example, ultra high performance LC (UHPLC or UPLC). In some examples, UPLC may be conducted using a reversed phase column chromatographic system, hydrophilic interaction chromatography (HILIC), ion exchange chromatography, or a mixed phase column chromatographic system.

Mass spectrometry is performed using a mass spectrometer that includes an ion source for ionizing the fractionated sample and creating charged molecules for further analysis. Ionization of the sample may be performed by, for example, heated electrospray ionization (HESI-II). The sample may be ionized in positive or negative mode.

After a sample has been ionized, the positively or negatively charged ions may be analyzed to determine a mass-to-charge ratio. Exemplary suitable analyzers for determining mass-to-charge ratios include quadrupole analyzers, ion trap analyzers, Fourier Transform Mass Spectrometry (FTMS) analyzers, and time of flight analyzers.

Analysis results may include data produced by tandem MS. In some examples, tandem MS may be accurate-mass tandem MS. For example, the accurate-mass tandem mass spectrometry may use a quadrupole time-of-flight (Q-TOF) analyzer. In other examples, tandem MS may be FTMS. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion.

Further, the level of the compound of the present invention may be measured indirectly, for example, by using an assay that measures the level of a compound (or compounds) that correlates with the level of the compound of the present invention that are desired to be measured using chromatography, mass spectrometry, enzyme-linked immunosorbent assay (ELIS A), antibody linkage, immunoblotting, immunohistochemistry (IHC), other immunochemical methods, or a combination thereof.

In a $3^{rd}$ embodiment, the compounds of the present invention can be used to assess (or aid in the assessment of) kidney function in a subject. It is understood that the compounds of the present invention can be used to assess any subject and includes the assessment of kidney function in an asymptomatic subject, in a subject at risk of CKD or AKI due to the presence of symptoms, or risk factors (e.g., hypertension, diabetes, family history of CKD, exposure to certain chemical/environmental conditions, etc.), and in a subject in response to a composition or to a therapeutic intervention (e.g., kidney transplant, lifestyle modification). It is further understood that a subject may undergo one or more assessments of kidney function.

In an exemplary method, assessing kidney function in a subject comprises determining the level of the compound of formula (I):

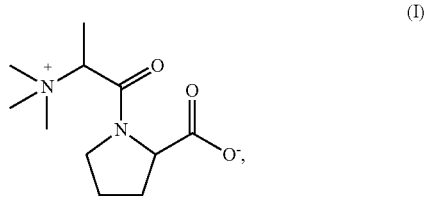

(I)

or a salt thereof, in a biological sample obtained from the subject, wherein an elevated level of the compound in the biological sample as compared to a reference level is indicative of reduced kidney function in the subject. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

When such a method is used to aid in assessing kidney function, the results of the method may be used along with other methods (or the results thereof) and/or patient metadata useful in the clinical determination of whether a subject has normal kidney function or impaired kidney function (which can result from an acute kidney injury (AKI) or CKD) as well as the level of kidney function (e.g., normal, mildly impaired, moderately impaired, severely impaired, end-stage kidney failure).

In certain embodiments, an accurate assessment of kidney function in a subject who is a potential kidney donor will aid a physician in determining whether the potential donor is suitable for donating a kidney.

In a $4^{th}$ embodiment, the compounds of the present invention can be used in a method of determining predisposition to developing reduced kidney function in a subject. In one embodiment, the method comprises determining the level of the compound of formula (I) or a salt thereof in a biological sample obtained from the subject, wherein an elevated level of the compound in the biological sample as compared to a reference level is indicative of predisposition to developing reduced kidney function in the subject. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In a $5^{th}$ embodiment, the compounds of the present invention can be used in a method classifying a subject according to level of kidney function (e.g., normal, mildly reduced, moderately reduced, severely reduced, end-stage kidney failure). In one embodiment, the method comprises determining the level of the compound of formula (I) or a salt thereof, in a biological sample obtained from the subject, wherein the level of the compound in the biological sample as compared to a reference level is used in classifying the subject according to level of kidney function. Any suitable methods can be used for determining the level of the compound. In one embodiment, the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

In a $6^{th}$ embodiment, the compounds of the present invention can be used in a method of monitoring kidney function in a subject. In one embodiment, the method comprises: (1) determining the level of the compound of formula (I) or a salt thereof, in a first biological sample obtained from the subject at a first time point; and (2) determining the level of the compound or a salt thereof in a second biological sample obtained from the subject at a second time, wherein the second time is later than the first time, and wherein a change in the level of the compound in the second biological sample from the level in the first biological sample is indicative of a change in kidney function. Any suitable methods can be used for determining the level of the compound. In one embodiment, the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

The change (if any) in the level(s) of the compound over time (i.e., in a first sample from a subject at a first time point compared to a second sample obtained from the subject at a second time point) may be indicative of altered kidney function in the patient over time. To characterize the kidney function of a subject over time, the level(s) of the compound in the first sample, the level(s) of the compound in the second sample, and/or the results of the comparison of the levels of the compound in the first and second samples may be compared to reference levels of the compound. If the comparisons indicate that the level(s) of the compound are increasing or decreasing over time (e.g., in the second sample as compared to the first sample) to become more similar to the low kidney function reference levels (or less similar to the high kidney function reference levels), then the results are indicative of declining kidney function. If the comparisons indicate that the level(s) of the compound are increasing or decreasing over time to become more similar to the high kidney function reference levels (or less similar to the low kidney function reference levels), then the results are indicative of normal kidney function. For example, a subject may have normal kidney function at a first time point (e.g., the level of the compound is similar to the high kidney function reference level or dissimilar to the low kidney function reference level) and remains in the normal range at a second time point (e.g., remains similar to the high kidney function reference level(s) or dissimilar to the low kidney function reference level(s)), indicating no change in kidney function. In another instance, the kidney function may be normal at a first time point (e.g., the level of the compound is similar to the high kidney function reference level(s) or dissimilar to the low kidney function reference level(s)) then decreases at a second time point yet remains in the normal range of kidney function, indicating that although still in the normal range, the kidney function decreased. In another illustration, a subject with borderline normal kidney function at a first time point may be diagnosed with CKD based on the level(s) of the biomarker(s) at the second time point indicating a worsening of kidney function in the subject.

The difference between the relative amount of the compound and the reference level may also be used to assess kidney function over time. For example, if the comparisons indicate that there is a larger difference between the level of the compound and the high kidney function reference levels (or a smaller difference between the level(s) of the compound and the low kidney function reference levels) over time, then the results are indicative of the patient developing declining kidney function.

After the first sample is obtained one or more additional samples may be obtained from the subject at a later point in time. In one aspect, the one or more additional samples are obtained 1, 2, 3, 4, 5, 6, or more days after the first sample. In another aspect, the one or more samples is obtained 1, 2, 3, 4, 5, 6, 7, 8, 9, 10, or more weeks after the first sample or after the initiation of treatment with the composition. In another aspect, the one or more additional samples may be obtained 1, 2, 3, 4, 5, 6, 7, 8, 9, 10, 1 1, 12, or more months after the first sample or after the initiation of treatment with the composition.

In certain embodiments, the level of the compound may be used to monitor kidney function in kidney transplant recipients.

In a $7^{th}$ embodiment, the compounds of the present invention can be used in a method for diagnosing or aid in diagnosing chronic kidney disease (CKD) in a subject. It will be understood that the compounds of the present invention can be used to diagnose or aid in diagnosing CKD in any subject, including asymptomatic subjects, those subjects presenting with one or more symptoms consistent with the presence of CKD and/or those subjects where CKD is probable (e.g., chronic illness, drug treatments, use of contrast imaging agents, etc.). In one embodiment, the method comprises determining the level of the compound of formula (I) or a salt thereof, in a biological sample obtained from the subject, wherein an elevated level of the compound in the biological sample as compared to a reference level is indicative of chronic kidney disease. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In certain embodiments, the compound of the present invention allows for the assessment of (or for aiding in the assessment of) kidney function to detect incipient CKD before CKD can be diagnosed using the current standards for determining kidney function (e.g., SCr, MDRDcr-eGFR, CKD-EPIcr-eGFR, cystatin C urine albumin and/or BUN measurements). Clinical measures may not be sufficiently sensitive to detect early changes in kidney function or may be inaccurate in certain subjects due to, for example, chronic illness, obesity, advanced age, vegetarian diet and/or generally reduced muscle mass. For example, in a subject with type 2 diabetes, the compound of the present invention may be used to diagnose or aid in the diagnosis of CKD. Accurate and early diagnosis of CKD may allow earlier therapeutic intervention which could delay or prevent the development of further kidney damage and more severe CKD.

In certain embodiments, after the level(s) of the compound of the formula (I) or (II) and optionally one or more additional biomarkers in the sample are determined, the level(s) are compared to CKD-positive and/or CKD-negative reference levels to diagnose or to aid in diagnosing whether the subject has CKD. Level(s) of the compound of the formula (I) or (II) and optionally one or more additional biomarkers reference levels (e.g., levels that are the same as the reference levels, substantially the same as the reference levels, slightly above and/or below the minimum and/or maximum of the reference levels, and/or within the range of the reference levels) are indicative of a diagnosis of CKD in the subject. Levels of the compound of formula (I) or (II) and optionally one or more additional biomarkers in a sample matching the CKD-negative reference levels (e.g., levels that are the same as the reference levels, substantially the same as the reference levels, slightly above and/or below the minimum and/or maximum of the reference levels, and/or within the range of the reference levels) are indicative of a diagnosis of no CKD in the subject. In addition, levels of the compound of the formula (I) or (II) and optionally one or more additional biomarkers that are differentially present (especially at a level that is statistically significant) in the sample as compared to CKD-negative reference levels are indicative of a diagnosis of CKD in the subject. Levels of the compound of the formula (I) or (II) and optionally one or more additional biomarkers that are differentially present (especially at a level that is statistically significant) in the sample as compared to CKD-positive reference levels are indicative of a diagnosis of no CKD in the subject.

The level(s) of the compound of the formula (I) or (II) and optionally one or more additional biomarkers may be compared to CKD-positive and/or CKD-negative reference levels using various techniques, including a simple comparison (e.g., a manual comparison) of the level(s) of the one or more biomarkers in the biological sample to CKD-positive and optionally CKD-negative reference levels. The level(s) of the compound of the formula (I) or (II) and/or one or more additional biomarkers in the biological sample may also be compared to CKD-positive and/or CKD-negative reference levels using one or more statistical analyses (e.g., t-test, Welch's T-test, Wilcoxon's rank sum test, correlation analysis, Random Forest, T-score, Z-score) or using a mathematical model (e.g., algorithm, statistical model).

For example, a mathematical model comprising a single algorithm or multiple algorithms may be used to assess kidney function in a subject. A mathematical model may be used to calculate an estimated glomerular filtration rate (eGFR). A mathematical model may also be used to determine whether a subject has CKD. A mathematical model may also be used to distinguish between CKD stages. An exemplary mathematical model may use the measured levels of the compound of the present invention and/or any number of additional biomarkers that are relevant in assessing kidney functions (for example, 2, 3, 5, 7, 9, etc.) from a subject to determine, using an algorithm or a series of algorithms based on mathematical relationships between the levels of the measured biomarkers, whether a subject has normal kidney function or CKD, whether a subject is predisposed to developing CKD, whether CKD is progressing in a subject, whether a subject has high stage (severe or very severe kidney function reduction), mid-stage (moderately reduced function) or low stage (mildly reduced function) CKD, etc. A different exemplary mathematical model may use the measured levels of the compound of present invention and/or any number of additional biomarkers (for example, 2, 3, 5, 7, 9, etc.) from a subject to classify a subject based on the level or stage of kidney function (e.g., high, moderate, low). In an example, the mathematical model generated for estimating GFR is used to assess kidney function, monitor kidney function, determine whether a subject has CKD or AKI, distinguish between CKD stages, and/or determine predisposition to CKD or AKI.

In certain embodiments, the methods of the present invention allow for the diagnosis of CKD in a subject not previously diagnosed with CKD. For example, in a subject with risk factors for CKD (e.g., age over 60 years, hypertension, diabetes, cardiovascular disease, and/or a family history of CKD, etc.), the biomarkers described herein may be used to diagnose or aid in the diagnosis of CKD.

In certain embodiments, the methods of the present invention allow for early detection and diagnosis before CKD can be diagnosed using the current standards for determining kidney function (e.g., SCr, MDRDcr-eGFR, CKD-EPIcr-eGFR, CKD-EPIcycys, urine albumin, cystatin C and/or BUN measurements). The early diagnosis of CKD may allow earlier therapeutic intervention which could delay or prevent the development of further kidney damage and more severe CKD.

In certain embodiments, the methods of the present invention may be used to diagnose or aid in diagnosing CKD in patients where the current standards for determining CKD (e.g., SCr, MDRDcr-eGFR, CKD-EPIcr-eGFR, CKD-EPIcycys, urine albumin, cystatin C, and/or BUN measurements) in subjects are inaccurate due to, for example, chronic illness, obesity, advanced age, vegetarian diet, and/or generally reduced muscle mass in the subject. For example, in a subject with type 2 diabetes, the biomarkers described herein may be used to diagnose or aid in the diagnosis of CKD.

When the method described above is used to aid in the diagnosis of CKD, the results of the method may be used along with other methods and measurements (or the results thereof) and/or patient metadata useful in the clinical determination of whether a subject has CKD. Methods useful in the clinical determination of whether a subject has CKD are known in the art. For example, methods useful in the clinical determination of whether a subject has CKD include, for example, SCr, BUN, eGFR, mGFR, urine albumin, and cystatin C. Other measurements useful in determining whether a subject has CKD include, for example $\beta$-2 microglobulin, $\beta$-TRACE, and/or 2-C-mannopyranosyl tryptophan. Patient metadata useful in the clinical determination of whether a subject has CKD include, for example, age, weight, gender, and race.

In an $8^{th}$ embodiment, the compounds of the present invention can be used in a method for monitoring the progression or regression of chronic kidney disease (CKD) in a subject. In one embodiment, the method comprises: (1) determining the level of the compound of formula (I) or a salt thereof, in a first biological sample obtained from the subject at a first time point; and (2) determining the level of the compound or a salt thereof in a second biological sample obtained from the subject at a second time, wherein the second time is later than the first time, and wherein a change in the level of the compound in the second biological sample from the level in the first biological sample is indicative of progression or regression of the disease in the subject. Any suitable methods can be used for determining the level of the compound. In one embodiment, the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

In a $9^{th}$ embodiment, the compounds of the present invention can be used in a method for diagnosing or aid in diagnosing acute kidney injury (AKI) in a subject. The method comprises determining the level of the compound of formula (I) or a salt thereof, in a biological sample obtained from the subject, wherein an elevated level of the compound in the biological sample as compared to a reference level is indicative of AKI. Any suitable methods can be used for determining the level of the compound. In one embodiment, the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

In a $10^{th}$ embodiment, the compounds of the present invention can be used in a method for monitoring the progression or regression of AKI in a subject. In one embodiment, the method comprises: (1) determining the level of the compound of formula (I) or a salt thereof, in a first biological sample obtained from the subject at a first time point; and (2) determining the level of the compound or a salt thereof in a second biological sample obtained from the subject at a second time, wherein the second time is later than the first time, and wherein a change in the level of the compound in the second biological sample from the level in the first biological sample is indicative of progression or regression of the disease in the subject. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In an $11^{th}$ embodiment, the compounds of the present invention can be used in a method of assessing kidney function in a subject in response to a composition or to a therapeutic intervention (e.g., kidney transplant, lifestyle modification). In one embodiment, the method comprises: determining the level of the compound of formula (I) or a salt thereof, in a biological sample obtained from a subject treated with the composition or a therapeutic intervention, wherein an elevated level of the compound in the biological sample as compared to the level of the compound in the subject without the treatment with the composition or the therapeutic intervention is indicative of reduced kidney function. Any suitable methods can be used for determining the level of the compound. In one embodiment, the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

The composition may be any composition, drug or therapeutic agent given to a subject to treat any disease or condition. The composition additionally may be any composition given to a patient having a disease or condition. In one embodiment, the composition is a contrast imaging agent. In another embodiment, the composition is a therapeutic agent, such as a chemotherapeutic agent. In another embodiment, the composition is an antibiotics.

In certain embodiments, the method described in the $11^{th}$ embodiment allows for assessment of the subject's response to a composition that alters kidney function as well as the assessment of the relative patient response to two or more compositions that alter kidney function. Such assessments may be used, for example, to select compositions for treating cancer for certain subjects, or to select subjects for a course of treatment or inclusion in clinical trial. Such assessments may also be used to monitor kidney function in response to a composition prior to, throughout and/or following (i.e., post-launch) the drug development process.

In certain embodiments, the methods of the present invention allow for the assessment of (or for aiding in the assessment of) kidney function in patients undergoing imaging tests using contrast agents where the contrast imaging agents may be toxic and, as a result, may cause kidney injury. For example in a patient with reduced kidney function (e.g., Stage 2 CKD or Stage 3 or Stage 3A CKD), an accurate measure of kidney function will help patients and clinicians assess the risk to benefit ratio of imaging tests and will allow for more informed decisions.

In a $12^{th}$ embodiment, the present invention provides a method for treating a subject having chronic kidney disease (CKD) comprising: (1) determining the level of the compound of formula (I) or a salt thereof, in a biological sample obtained from the subject; and (2) administering to the subject an effective therapy suitable for treating chronic kidney disease if the subject has an elevated level of the compound as compared to a reference level. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In a $13^{th}$ embodiment, the present invention provides a method for treating a subject having chronic kidney disease (CKD) comprising administering to the subject an effective therapy suitable for treating chronic kidney disease, wherein the subject has an elevated level of the compound of formula (I), or a salt thereof, as compared to a reference level. In one embodiment, the level of the compound is determined using chromatography, mass spectrometry, enzyme-linked immunosorbent assay (ELIS A), antibody linkage, immunoblotting, immunohistochemistry (IHC), other immunochemical methods, or a combination thereof.

Chronic kidney disease often is caused by underlying disease(s) or condition(s). For example, high blood pressure (hypertension) or diabetes can lead to chronic kidney disease. Other causes for chronic kidney disease may include: (1) kidney diseases and infections, such as polycystic kidney disease, pyelonephritis, and glomerulonephritis; (2) a narrowed or blocked renal artery; (3) prolonged obstruction of the urinary tract, from conditions such as enlarged prostate, kidney stones and cancers; (4) vesicoureteral reflux, a condition that causes urine to back up into kidney; and (5) long-term use of medicines (e.g., nonsteroidal anti-inflammatory drugs (NSAIDs), such as celecoxib and ibuprofen) that can damage the kidneys.

Chronic kidney disease is often treated with effective treatments for the underlying condition or disease that caused CKD. In certain embodiments, CKD is caused by diabetes and the method of treating CKD in the $12^{th}$ or $13^{th}$ embodiment comprises administering to the subject an effective therapy suitable for treating diabetes. Diabetes can be treated with an antidiabetic agent. Exemplary antidiabetic agents include, but are not limited to, metformin, pioglitazone, rosiglitazone, acarbose, tetrahydrolipstatin, phentermine/topiramate, bupropion/naltrexone, lorcaserin, liraglutide, and canagliflozin. In certain embodiments, diabetes can be treated by lifestyle modification. Exemplary lifestyle modification includes, but is not limited to, dietary modification and/or an increase in activity or exercise. Dietary modification may include, for example, limiting calories intake, serving sizes, sugar and starchy carbohydrates content and/or choosing foods that are low in fat and calories and high in fiber.

In certain embodiments, CKD is caused by high blood pressure (hypertension) and the method of treating CKD in the $12^{th}$ or $13^{th}$ embodiment comprises administering to the subject an effective therapy suitable for treating high blood pressure. In certain embodiments, the method described in the $12^{th}$ or $13^{th}$ embodiment comprises administering to the subject an effective amount of a therapeutic agent to lower the blood pressure. Exemplary therapeutic agents include, but are not limited to angiotensin-converting enzyme (ACE) inhibitors or angiotensin II receptor blockers (ARBs). Suitable ACE inhibitors include, but are not limited to, benazepril, captopril, enalapril, fosinopril, lisinopril, perindopril, quinapril, ramipril and trandolapril. Suitable ARBs include, but are not limited to, candesartan, eprosartan, irbesartan, losartan, olmesartan, telmisartan and valsartan. In certain embodiments, diuretics and/or low-salt diet are also used to lower the blood pressure.

In certain embodiments, the treatment of CKD described in the $12^{th}$ or $13^{th}$ embodiment includes lifestyle modification, such as dietary modification and/or an increase in activity or exercise. Dietary modification may include low salt diet, choosing food with low potassium content and/or limiting the amount of daily protein intake.

In certain embodiments, the treatment of CKD described in the $12^{th}$ or $13^{th}$ embodiment includes dietary supplement(s), such as vitamin D, iron, calcium, potassium, or a combination thereof.

In certain embodiments, CKD can progress to end-stage kidney failure, which can be treated by dialysis or kidney transplant.

In a $14^{th}$ embodiment, the present invention provides a method for treating a subject suffering from an acute kidney injury comprising: (1) determining the level of the compound of formula (I) or a salt thereof, in a biological sample obtained from the subject; and (2) administering to the subject an effective therapy suitable for treating the acute kidney injury if the subject has an elevated level of the compound as compared to a reference level. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In a 15th embodiment, the present invention provides a method for treating a subject suffering from an acute kidney injury comprising administering to the subject an effective therapy suitable for treating the acute kidney injury, wherein the subject has an elevated level of the compound of formula (I), or a salt thereof, as compared to a reference level. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

Acute kidney injury (AKI) can be caused by various conditions, such as a condition that slows blood flow to the kidney, direct damage to the kidney and/or blocked ureters. Conditions that impair blood flow to the kidneys include, but are not limited to, blood or fluid loss, blood pressure medications, heart attack, heart disease, infection, liver failure, use of aspirin, ibuprofen (Advil, Motrin IB, others), naproxen (Aleve, others) or related drugs, severe allergic reaction (anaphylaxis), severe burns and severe dehydration. Diseases, conditions and agents that may cause direct damage to the kidneys include, but are not limited to, blood clots in the veins and arteries in and around the kidneys, cholesterol deposits that block blood flow in the kidneys, glomerulonephritis, inflammation of the tiny filters in the kidneys (glomeruli), hemolytic uremic syndrome, a condition that results from premature destruction of red blood cells, infection, lupus, an immune system disorder causing glomerulonephritis, medications, such as certain chemotherapy drugs, antibiotics, dyes used during imaging tests and zoledronic acid (Reclast, Zometa), used to treat osteoporosis and high blood calcium levels (hypercalcemia), multiple myeloma, a cancer of the plasma cells, scleroderma, a group of rare diseases affecting the skin and connective tissues, thrombotic thrombocytopenic purpura, a rare blood disorder, toxins, such as alcohol, heavy metals and cocaine, and vasculitis, an inflammation of blood vessels. Diseases and conditions that can cause urinary blockage and lead to AKI include, but are not limited to, bladder cancer, blood clots in the urinary tract, cervical cancer, colon cancer, enlarged prostate, kidney stones, nerve damage involving the nerves that control the bladder and prostate cancer.

AKI is often treated with an effective therapy for the underlying causes. In certain embodiments, AKI is caused by medications, such as chemotherapeutic agents, and the method of treating AKI in a subject comprises stopping the administration of the medication to subject or reducing the dosage of the medication (e.g., chemotherapeutic agent) administered to the subject.

In certain embodiments, AKI is caused by hypertension or diabetes and the method of treating AKI in a subject comprises administering an effective therapy for hypertension or diabetes described above in the 12th or 13th embodiment.

In certain embodiments, the method of treating AKI in a subject comprises lifestyle modification, such as dietary modification and/or an increase in activity or exercise. Dietary modification may include low salt diet, choosing food with low potassium content and/or limiting the amount of daily protein intake.

In certain embodiments, AKI is treated by dialysis or kidney transplant.

In a 16th embodiment, the present invention provides a method for calculating the estimated glomerular filtration rate (eGFR) in a patient comprising the steps of: (1) determining the level of the compound of formula (I) or a salt thereof, in a biological sample obtained from the subject; and (2) calculating the eGFR using an algorithm that utilizes the measured level of the compound, wherein the algorithm is developed using GFR measured using an exogenous filtration marker. Any suitable methods can be used for determining the level of the compound. In one embodiment, the level of the compound is determined using chromatography, mass spectrometry, enzyme-linked immunosorbent assay (ELISA), antibody linkage, immunoblotting, immunohistochemistry (IHC), other immunochemical methods, or a combination thereof.

In certain embodiments, the eGFR is calculated using one or more additional biomarkers relevant for the assessment of kidney function. In one embodiment, the one or more additional biomarkers are selected from pseudouridine, N-acetylthreonine, 2-C-mannopyranosyl tryptophan, N-acetylserine, N-acetyl alanine, N6-carbamoylthreonyl adenosine, 4-acetamidobutanoate, erythritol, myo-inositol, erythronate, urea, arabitol, N2,N2-dimethylguanosine, N1-methyladenosine, 3-methylglutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, and p-cresol sulfate. In another embodiment, the eGFR algorithm further utilizes serum cystatin C levels. In yet another embodiment, the eGFR algorithm further utilizes one or more demographic parameters selected from the group consisting of age, sex and race.

In a 17th embodiment, for methods described in the 2nd-16th embodiments, the compound of formula (I) is represented by formula (II):

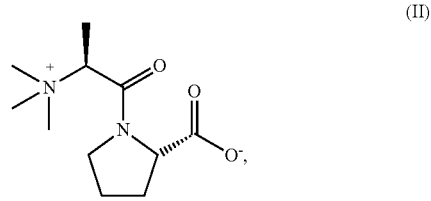

or a salt thereof.

In an 18th embodiment, for methods described in the 2nd-16th embodiments, the level of the compound is determined by tandem liquid chromatography-mass spectrometry (LC-MS/MS).

In a 19th embodiment, the methods described in the 2nd-18th embodiments further comprise using the determined level of the compound in a mathematical model to assess kidney function.

In a 20th embodiment, the methods described in the 2nd-19th embodiments further comprise analyzing the biological sample to determine the level of one or more additional biomarkers relevant for the assessment of kidney function. The one or more biomarkers may be selected from the group consisting of the following biomarkers: pseudouridine, N-acetylthreonine, 2-C-mannopyranosyl tryptophan, N-acetylserine, N-acetylalanine, N6-carbamoylthreonyladenosine, 4-acetamidobutanoate, erythritol, myo-inositol, erythronate, urea, arabitol, N2,N2-dimethylguanosine, N1-methyladenosine, 3-methyl glutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, and p-cresol sulfate, and combinations thereof.

In certain embodiments, the levels of two, three, four, five, six, seven, eight, nine, ten, eleven, twelve or more additional biomarkers are determined in the method described in the 20th embodiment.

In certain embodiments, for the method described in the 20th embodiment, the one or more additional biomarkers are selected from the group consisting of pseudouridine, N-acetylthreonine, tryptophan, phenylacetylglutamine, 2-C-mannopyranosyl tryptophan, kynurenine, myo-inositol, and creatinine.

In certain embodiments, for the method described in the 20th embodiment, the one or more additional biomarkers are selected from the group consisting of pseudouridine, 2-C-mannopyranosyl tryptophan, tryptophan, N-acetylthreonine, and creatinine In certain embodiments, for the method described in the 20th embodiment, the one or more additional biomarkers are selected from the group consisting of pseudouridine, N-acetylthreonine, tryptophan, phenylacetylglutamine, and creatinine.

In certain embodiments, for the method described in the 20th embodiment, the one or more additional biomarkers are selected from the group consisting of N-acetylthreonine, myo-inositol, 2-C-mannopyranosyl tryptophan, and creatinine.

In certain embodiments, for the method described in the 20th embodiment, the one or more additional biomarkers are selected from the group consisting of N-acetylthreonine, myo-inositol, kynurenine, and creatinine.

In certain embodiments, for the method described in the 20th embodiment, the one or more additional biomarkers are selected from the group consisting of pseudouridine, 2-C-mannopyranosyl tryptophan, N-acetylthreonine, and myo-inositol.

In certain embodiments, for the method described in the 20th embodiment, the one or more additional biomarkers are selected from the group consisting of pseudouridine, N-acetylthreonine, myo-inositol, and creatinine.

In certain embodiments, the method described in the 20th embodiment further comprises analyzing the biological sample to determine the level of pseudouridine, N-acetylthreonine, tryptophan, phenylacetylglutamine and creatinine.

Determining levels of the compound of the present invention and one or more additional biomarkers may allow greater sensitivity and specificity in the described methods. For example, pair-wise analysis of two biomarkers or ratios of the levels of certain biomarkers (and non-biomarker compounds) in biological samples may allow greater sensitivity and specificity in assessing kidney function and aiding in the assessment of kidney function.

The level(s) of the compound of formula (I) or (II) and/or the one or more additional biomarkers may be compared to kidney function reference levels using various techniques, including a simple comparison (e.g., a manual comparison). The level(s) of the compound of formula (I) or (II) and/or the one or more additional biomarkers in the biological sample may also be compared to reference levels using one or more statistical analyses (e.g., t-test, Welch's T-test, Wilcoxon's rank sum test, correlation analysis, Random Forest, T-score, Z-score) or using a mathematical model (e.g., algorithm, statistical model). For example, a mathematical model comprising a single algorithm or multiple algorithms may be used to assess kidney function in a subject.

The results of the method may be used along with other methods and measurements (or the results thereof) useful in the assessment of kidney function in a subject. For example, clinical parameters such as BUN, SCr, and/or urine albumin measurements; markers of kidney function such as β-2 microglobulin, β-TRACE, 2-C-mannopyranosyl tryptophan; as well as patient information such as, for example, family history of CKD or other risk factors can be used with the biomarkers.

In certain embodiments, the level of the compound of the present invention and/or one or more additional biomarkers can be used in a mathematical or statistical model or formula to provide a physician with a numerical score ("Kidney Function Score") indicating the level of kidney function and/or the probability that a subject has compromised kidney function which may indicate AKI or CKD. The score is based upon clinically significantly changed reference level(s) for a biomarker and/or combination of biomarkers. The reference level can be derived from an algorithm or computed from indices for impaired GFR. Methods for determining a subject's Kidney Function Score may comprise comparing the level(s) of the one or more kidney function biomarkers in the sample to kidney function reference levels of the one or more biomarkers in order to determine the subject's Kidney Function Score. The method may employ any number of biomarkers selected from the following list: pseudouridine, N-acetylthreonine, 2-C-mannopyranosyl tryptophan, N-acetylserine, N-acetylalanine, N6-carbamoylthreonyladeno sine, 4-acetamidobutanoate, erythritol, myo-inositol, erythronate, urea, arabitol, N2,N2-dimethylguanosine, N1-methyladenosine, 3-methyl glutarylcarnitine, S-adenosylhomocysteine, N-acetylmethionine, N6-acetyllysine, kynurenine, arabonate, succinylcamitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, and p-cresol sulfate. Multiple biomarkers may be correlated with kidney function, by any method, including statistical methods such as regression analysis.

The Kidney Function Score can be used to place the subject in the range of kidney function from normal (i.e. no kidney function impairment) to mildly reduced, moderately reduced, severely reduced, or end-stage kidney failure. Non-limiting example uses of the Kidney Function Score include: assessment of kidney function; estimation of GFR; classification of kidney function; susceptibility to developing CKD; susceptibility to developing AKI; diagnosis and stage of CKD; monitoring CKD progression by periodic determination and monitoring of the Kidney Function Score; monitoring the kidney function status of kidney transplant recipients; determining a response to therapeutic intervention; evaluating drug efficacy; and determining tolerance of therapeutic and/or contrast imaging agents.

In certain embodiments, for the methods of the present invention described herein, the biological sample is blood, blood plasma, serum, saliva or urine. In one embodiment, the biological sample is blood plasma. In another embodiment, the biological sample is serum.

In certain embodiments, for the methods of the present invention described herein, the biological sample is obtained from the subject prior to treatment with an agent that allows direct measurement of glomerular filtration rate.

In certain embodiments, for the methods of the present invention described herein, the subject is a human.

In certain embodiments, for the methods of the present invention described herein, the subject has no symptoms of impaired kidney function or has no known risk factors for impaired kidney function. In other embodiments, the subject exhibits risk factors for developing chronic kidney disease (e.g., age over 60, hypertension, diabetes, cardiovascular disease, family history of CKD). In certain embodiments, the subject has been previously diagnosed with hypertension or diabetes. In certain embodiments, the subject a family history of chronic kidney disease. In certain embodiments, the subject has symptoms of impaired kidney function. In certain embodiments, the subject is one for whom kidney function assessment using conventional methods is difficult.

In certain embodiments, the subject is selected from the group consisting of the following: obese, very lean, vegetarian, chronically ill, and elderly.

In certain embodiments, the subject is a candidate to be a kidney donor.

In certain embodiments, the subject has been treated with or is being considered for treatment with an agent that may have a toxic effect on the kidneys. In one embodiment, the agent is contrast imaging agent. In another embodiment, the agent is a therapeutic agent for treating a disease or condition, such as a chemotherapeutic agent. In yet another embodiment, the agent is an antibiotic.

In certain embodiments, the methods could be used to monitor kidney function in subjects having CKD or subjects suspected of being predisposed to developing CKD (e.g., at risk subjects due to family history of CKD, drug therapy, chronic illness, etc.). In one example, the compound of the present invention may be used to monitor kidney function in subjects not having CKD. For example, in a subject suspected of being predisposed to developing CKD, the biomarkers described herein may be used to monitor the development of CKD.

Kits

The present invention includes kits for measuring the level of the compound of formula (I) or formula (II) in a biological sample.

The kits of the present invention may be used for assessing or monitoring kidney function in a subject, determining predisposition to developing reduced kidney function, classifying a subject according to level of kidney function, diagnosing or monitoring chronic kidney disease, estimating GFR in a subject.

In certain embodiments, the kit of the present invention comprises a compound of formula (I) or a salt thereof. In one embodiment, the kit of the present invention comprises a compound of formula (II) or a salt thereof.

In certain embodiments, the kit of the present invention comprises a compound of formula (I) or a salt thereof and instructions for measuring the level of the compound of formula (I) in a biological sample. In one embodiment, the kit comprises a compound of formula (II) or a salt thereof and instructions for measuring the level of the compound of formula (II) in a biological sample.

In certain embodiments, the kit of the present invention can comprise a labeled compound (e.g., an internal standard) or an agent capable of detecting the compound of formula (I) or (II) in a biological sample.

In certain embodiments, the kit of the present invention can comprise a labeled compound (e.g., an internal standard) or an agent capable of detecting the compound of formula (I) or (II) in a biological sample and instructions for measuring the level of the compound of formula (I) or (II) in a biological sample.

In one embodiment, the internal standard in the kit described above is a labeled compound of formula (I) or formula (II). In another embodiment, the internal standard in the kit described above is N,N,N-Trimethyl-L-Alanyl-L-Proline-$^{13}C_3$ ($^{13}C_3$-L,L-TMAP).

In one embodiment, the kit of the present invention comprises unlabeled compound of formula (I) or a salt thereof, a labeled compound of formula (I) as an internal standard and instructions for measuring the level of the compound of formula (I) in a biological sample.

In another embodiment, the kit of the present invention comprises unlabeled compound of formula (II) or a salt thereof, a labeled compound of formula (II) as an internal standard and instructions for measuring the level of the compound of formula (II) in a biological sample. In one embodiment, the labeled compound of formula (II) is N,N,N-Trimethyl-$^{13}C_3$-L-Alanyl-L-Proline ($^{13}C_3$-L,L-TMAP).

In another embodiment, the $^{13}C_3$-L,L-TMAP described herein is represented by the following formula:

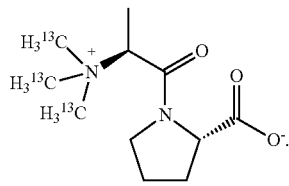

In certain embodiments, the kit of the present invention can comprise a labeled compound (e.g., an internal standard) or an agent capable of detecting the compound of formula (I) or (II) in a biological sample and means for determining the amount of the compound in the sample (e.g., an antibody against the compound of formula (I) or (II)).

In certain embodiments, the amount of the compound of formula (I) or (II) in a biological sample can be determined by chromatography, mass spectrometry, enzyme-linked immunosorbent assay (ELISA), antibody linkage, immunoblotting, immunohistochemistry (IHC), other immunochemical methods, or a combination thereof using the kit of the present invention described herein. In certain embodiments, the amount of the compound of formula (I) or (II) in a biological sample can be determined by chromatography, mass spectrometry, or a combination thereof. In certain embodiments, the amount of the compound of formula (I) or (II) in a biological sample can be determined by LC-MS using the kit of the present invention.

The kit may also comprise, e.g., a buffering agent, a preservative, or a stabilizing agent. The kit may also contain a control sample or a series of control samples which can be assayed and compared to the test sample. Each component of the kit is usually enclosed within an individual container and all of the various containers are within a single package along with instructions for determining whether the tested subject is suffering from or is at risk of developing a disorder associated with the relevant small molecule.

In a 21$^{st}$ embodiment, the kit of the present invention comprises a compound of the present invention described above (e.g., a compound of formula (I) or (II), or a salt thereof), and instructions for assessing or monitoring kidney function in a subject based on the level of the compound detected in a biological sample obtained from the subject.

In 22$^{nd}$ embodiment, the kit of the present invention comprises a compound of the present invention described above (e.g., a compound of formula (I) or (II), or a salt thereof), and instructions for determining predisposition to developing reduced kidney function in a subject based on the level of the compound detected in a biological sample obtained from the subject.

In a 23$^{rd}$ embodiment, the kit of the present invention comprises a compound of the present invention described above (e.g., a compound of formula (I) or (II), or a salt thereof), and instructions for classifying a subject according to level of kidney function based on the level of the compound detected in a biological sample obtained from the subject.

In a 24$^{th}$ embodiment, the kit of the present invention comprises a compound of the present invention described above (e.g., a compound of formula (I) or (II), or a salt thereof), and instructions for diagnosing or monitoring chronic kidney disease (CKD) in a subject based on the level of the compound detected in a biological sample obtained from the subject.

In a 25$^{th}$ embodiment, the kit of the present invention comprises a compound of the present invention described above (e.g., a compound of formula (I) or (II), or a salt thereof), and instructions for diagnosing or monitoring acute kidney injury (AKI) in a subject based on the level of the compound detected in a biological sample obtained from the subject.

In a 26$^{th}$ embodiment, the kit of the present invention comprises a compound of the present invention described above (e.g., a compound of formula (I) or (II), or a salt thereof), and instructions for estimating GFR in a subject based on the level of the compound detected in a biological sample obtained from the subject.

In certain embodiments, for the kit described in the 21$^{st}$-26$^{th}$ embodiments, the compound of formula (I) or (II) is isotopically labeled. In one embodiment, the compound of formula (I) or (II) is radiolabeled, for example, with tritium ($^3$H) or carbon 14 ($^{14}$C). In another embodiment, the compound of formula (I) or (II) is deuterated, labeled with carbon 13 ($^{13}$C), or nitrogen 15 ($^{15}$N), or a combination thereof. In an example, the labeled compound of formula (II) is N,N,N-Trimethyl-$^{13}$C$_3$-L-Alanyl-L-Proline ($^{13}$C$_3$-L,L-TMAP), which can be used as an internal standard.

The present invention also provides kits comprising antibodies or antibody fragments that specifically binds to compound of formula (I) or (II) or a salt (e.g., a pharmaceutically acceptable salt) thereof described above for assessing or monitoring kidney function in a subject, determining predisposition to developing reduced kidney function, classifying a subject according to level of kidney function, diagnosing or monitoring chronic kidney disease, estimating GFR in a subject. In certain embodiments, the kits of the present invention comprises antibody derivatives, such as a polypeptide comprising the V$_H$ and V$_L$ sequences of the antibody described above. In one embodiment, the polypetide is a fusion protein.

In a 27$^{th}$ embodiment, the kit of the present invention comprises an antibody, an antibody fragment or an antibody derivative described above, and instructions for assessing or monitoring kidney function in a subject based on the level of the compound detected in a biological sample obtained from the subject.

In a 28$^{th}$ embodiment, the kit of the present invention comprises an antibody, an antibody fragment or an antibody derivative described above, and instructions for determining predisposition to developing reduced kidney function in a subject based on the level of the compound detected in a biological sample obtained from the subject.

In a 29$^{th}$ embodiment, the kit of the present invention comprises an antibody, an antibody fragment or an antibody derivative described above, and instructions for classifying a subject according to level of kidney function based on the level of the compound detected in a biological sample obtained from the subject.

In a 30$^{th}$ embodiment, the kit of the present invention comprises an antibody, an antibody fragment or an antibody derivative described above, and instructions for diagnosing or monitoring chronic kidney disease (CKD) in a subject based on the level of the compound detected in a biological sample obtained from the subject.

In a 31$^{st}$ embodiment, the kit of the present invention comprises an antibody, an antibody fragment or an antibody derivative described above, and instructions for diagnosing or monitoring acute kidney injury (AKI) in a subject based on the level of the compound detected in a biological sample obtained from the subject.

In a 32$^{nd}$ embodiment, the kit of the present invention comprises an antibody, an antibody fragment or an antibody derivative described above, and instructions for estimating GFR in a subject based on the level of the compound detected in a biological sample obtained from the subject.

In certain embodiments, the kit described above (e.g., the kit described in the 21$^{st}$-26$^{th}$ embodiments) comprises one or more additional biomarkers other than the compound, wherein the one or more additional biomarkers are relevant to the assessment of kidney function. Any biomarkers described herein can be used in the kits of the present invention.

In certain embodiments, the kit described above (e.g., the kit described in the 27$^{st}$-32$^{nd}$ embodiments) comprises one or more additional biomarkers, wherein the one or more additional biomarkers are relevant to the assessment of kidney function. Any biomarkers described herein can be used in the kits of the present invention.

In various embodiments, the one or more additional biomarkers are selected from the group consisting of pseudouridine, N-acetylthreonine, 2-C-mannopyranosyl tryptophan, N-acetylserine, N-acetylalanine, N6-carbamoyl-threonyl adenosine, 4-acetamidobutanoate, erythritol, myo-inositol, erythronate, urea, arabitol, N2,N2-dimethylguanosine, N1-methyladenosine, 3-methylglutarylcarnitine, S-adenosylhomocysteine, N-acetylmethionine, N6-acetylly-sine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate, and p-cresol sulfate. In one embodiment, the additional biomarkers are selected from the group consisting of pseudouridine, N-acetylthreonine, tryptophan, phenylacetylglutamine, 2-C-mannopyranosyl tryptophan, kynurenine, myo-inositol, and creatinine. In another embodiment, the additional biomarkers are selected from the group consisting of pseudouridine, N-acetylthreonine, tryptophan, phenylacetylglutamine and creatinine.

In certain embodiments, the one of more additional biomarkers are selected from the group consisting of N-acetylthreonine, myo-inositol, 2-C-mannopyranosyl tryptophan, and creatinine.

In certain embodiments, the one of more additional biomarkers are selected from the group consisting of N-acetylthreonine, myo-inositol, kynurenine, and creatinine.

In certain embodiments, the one of more additional biomarkers are selected from the group consisting of pseudouridine, 2-C-mannopyranosyl tryptophan, N-acetylthreonine, and myo-inositol.

In certain embodiments, the one of more additional biomarkers are selected from the group consisting of pseudouridine, N-acetylthreonine, myo-inositol, and creatinine.

In certain embodiment, the kits of the present invention comprises a compound of the present invention described above (compound of formula (I) or (II) or a salt thereof), pseudouridine, N-acetylthreonine, tryptophan, phenylacetylglutamine and creatinine.

Methods of Preparation

One can refer to the following references for suitable methods of synthesis as described in March, *Advanced Organic Chemistry*, 3rd edition, John Wiley & Sons, 1985 or Greene and Wuts *Protective groups in organic synthesis* 2*nd* edition, John Wiley & sons 1991 and as in Richard Larock, *comprehensive organic transformations*, 4*th* edition, VCH publishers Inc, 1989.

In one embodiment, the compound of formula (I) can be prepared by reacting a compound of formula (III):

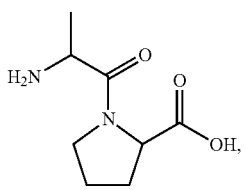

(III)

or a salt thereof, with a methylation reagent.

In another embodiment, the present invention provides a method of preparing a compound of formula (II) comprising reacting a compound of formula (IV):

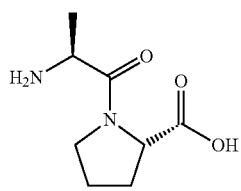

(IV)

or a salt thereof, with a methylation reagent.

In another embodiment, the compound of formula (I) can be prepared by reacting a compound of formula (V):

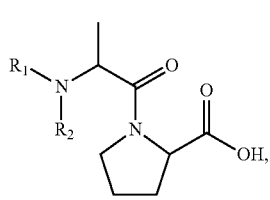

(V)

or a salt thereof, with a methylation reagent, wherein $R_1$ is H, and $R_2$ is $CH_3$; or $R_1$ and $R_2$ are both $CH_3$.

In another embodiment, the compound of formula (II) can be prepared by reacting a compound of formula (VI):

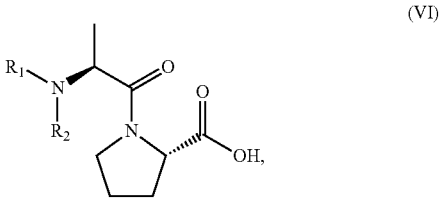

(VI)

or a salt thereof, with a methylation reagent, wherein $R_1$ is H, and $R_2$ is $CH_3$; or $R_1$ and $R_2$ are both $CH_3$.

In certain embodiments, the methylation reagent in the methods described above is $CH_3X$ or $(CH_3)_2SO_4$, wherein X is Cl, Br, I or $OSO_2CF_3$. In another embodiment, the methylation reagent is iodomethane ($CH_3I$).

In certain embodiments, the methylation reaction in the methods described above is carried out in the presence of a base. Any suitable base can used. Exemplary bases include, but are not limited to, potassium carbonate, sodium carbonate, and sodium hydroxide.

In one embodiment, the methylation reaction in the methods described above is carried out in the presence of silver oxide.

In another embodiment, the methylation reaction in the methods described above is carried out in the presence of potassium carbonate.

In certain embodiments, the methylation reaction for the methods described above is carried out in a mixture of water and an organic solvent or in 100% water. Any suitable organic solvents can be used, which may include, but are not limited to, methanol, ethanol, acetone, acetonitrile, dichloromethane, dimethylformamide (DMF), dimethylsulfoxide etc. For example, the methylation reaction is carried out in a mixture of methanol and water. The volume ratio of methanol to water can be from 1:10 to 10:1, 1:5 to 5:1; 5:1 to 1:1, 4:1 to 1:1. In one embodiment, the volume ratio of methanol to water is about 4:1.

EXAMPLES

Material and Methods

Reagents and Instruments

Silver oxide, potassium carbonate, iodomethane, and mass spectrometric grade (98%) formic acid were obtained from Sigma-Aldrich; HPLC grade methanol and water from Fisher Scientific; Deuterium oxide (99.8%) from Acros; L-Alanyl-L-proline from Tokyo Chemical Industry. A Fisher Scientific vortex mixer was used for mixing and a Sorvall Legend Micro 21R microcentrifuge used for centrifugation of 1.5 mL Eppendorf tubes. A Corning Laboratory stirrer was used for mixing chemical reactions. Human plasma (K2-EDTA) was obtained from Bioreclamation and stored at −80° C. An Argonaut SPE DRY™ 96 DUAL evaporator was used for solvent evaporation.

Chromatography

A Waters Acquity UPLC system equipped with a binary solvent manager, a refrigerated sample manager (set at 12° C.), and a column manager (set at 40° C.) was used for liquid chromatography with a reversed phase column (Waters ACQUITY UPLC® BEH C18, 1.7 µm, 2.1×100 mm). Mobile phase A was 0.1% formic acid in water and mobile phase B was 0.1% formic acid in methanol. For deuterium exchange experiments, mobile phase A was 0.1% formic acid in deuterium oxide instead. Linear gradient elution was carried out with an initial condition of 0% mobile phase B, which was held for 2.00 min. Mobile phase B was then increased to 98% in 0.50 min and maintained for 0.90 min. Mobile phase B reverted to 0% in 0.10 min for equilibration for next injection. The flow rate was 350 µL/min and the total run time was 4.50 min. A loop fixed aliquot of 5.0 µL of the final sample solution was injected for each sample. The eluent was directly introduced into the electrospray source of a mass spectrometer. Strong needle wash was neat methanol and weak needle wash was a mixture of methanol and water (0.5:99.5). Seal wash was a mixture of methanol and water (10:90).

Mass Spectrometry

A Thermo Scientific Orbitrap Elite mass spectrometer equipped with a heated electrospray ionization (HESI-II) probe was used in positive mode for this study. The instrument was controlled by Orbitrap Elite™ 2.7 and XCalibur™ 2.2 software. The heated electrospray source was set with heater temperature at 430° C., sheath gas at 30, and auxiliary gas flow rates at 12, sweep gas at 0, ion spray voltage at 4.20 kV, capillary temperature at 350° C., and S-lens RF level at 65%. A resolution of 30,000 was used to collect full scan FTMS (Fourier Transform Mass Spectrometry) spectra with mass range between m/z 100 and 300. For all MS fragmentation experiments, a resolution of 15,000 was used along with activation Q of 0.250 and activation time of 10.0 ms. The normalized collision energy for $MS^2$ experiment was 31.0 eV with an isolation width of 1.0 m/z and scan range between m/z 60 and 240. For the $MS^3$ experiment of m/z 229.1547/142.0860 (or 230.1610/143.0925 for deuterium exchange), normalized collision energy was 31.0 and 25.0 eV for first and second stage fragmentation, respectively, with isolation width of m/z 2.0 for both stages and scan range between m/z 50 and 240. For the $MS^3$ experiment of m/z 229.1547/170.0810 (or 230.1610/171.0878 for deuterium exchange), normalized collision energy was 31.0 and 30.0 eV for first and second stage fragmentation, respectively. The isolation width was m/z 3.0 and 2.0 for first and second stage fragmentation, respectively, and scan range between m/z 50 and 240. For the $MS^4$ experiment of m/z 229.1547/142.0860/114.0911 (or 230.1610/143.0925/115.0976 for deuterium exchange), normalized collision energy was 31.0, 20.0, and 20.0 eV for first to third stage fragmentation. Isolation width was m/z 2.0 for all the three stages and scan range between m/z 50 to 240.

Example 1

Synthesis of N,N,N-Trimethyl-L-Alanyl-L-Proline (TMAP)

Method 1. In a 4 mL glass vial with a magnetic stir bar were added L-alanyl-L-proline (20.0 mg, 0.108 mmol), silver oxide (100 mg, 0.432 mmol), and 1.0 mL of methanol/water (4:1). The mixture was stirred on a magnetic stirrer at room temperature and 75 µL of iodomethane (171 mg, 1.2 mmol) added. The vial was loosely capped and the mixture stirred overnight at room temperature in dark. The resulting mixture was evaporated to dryness under a gentle stream of nitrogen at 40° C. Water (1.0 mL) was added to the residue and the mixture was sonicated for 2 min. The mixture was then transferred to a 1.5 mL Eppendorf tube and centrifuged at room temperature for 10 min at 14,000 rpm. The clear supernatant was diluted 10,000 fold with 0.1% formic acid in water and transferred to a sample vial for LC/MS analysis. To synthesize N,N,N-Trimethyl-$^{13}C_3$-L-Alanyl-L-Proline ($^{13}C_3$-L,L-TMAP), the same synthesis procedure was used except that iodomethane was replaced with iodomethane-$^{13}C$.

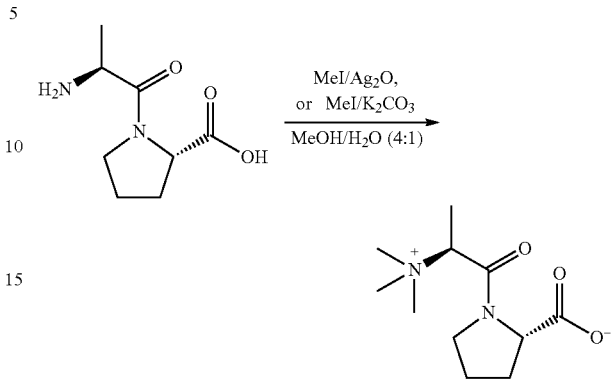

Figure 18A:
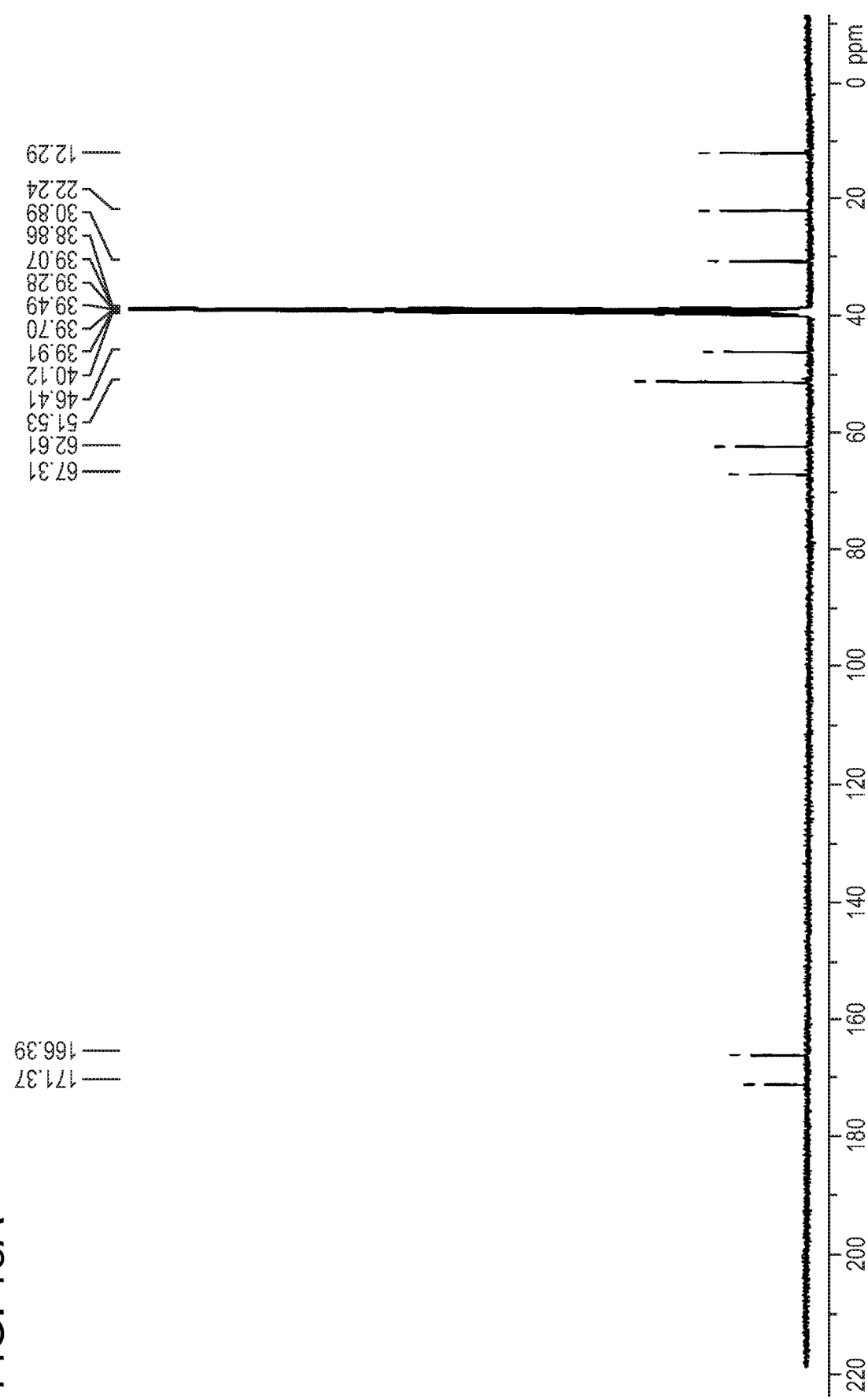
FIGS. 18A and 18B show $^{13}$C-NMR spectra of the unlabeled TMAP (FIG. 18A) and $^{13}$C-labeled TMAP (FIG. 18B).
Figure 18B:
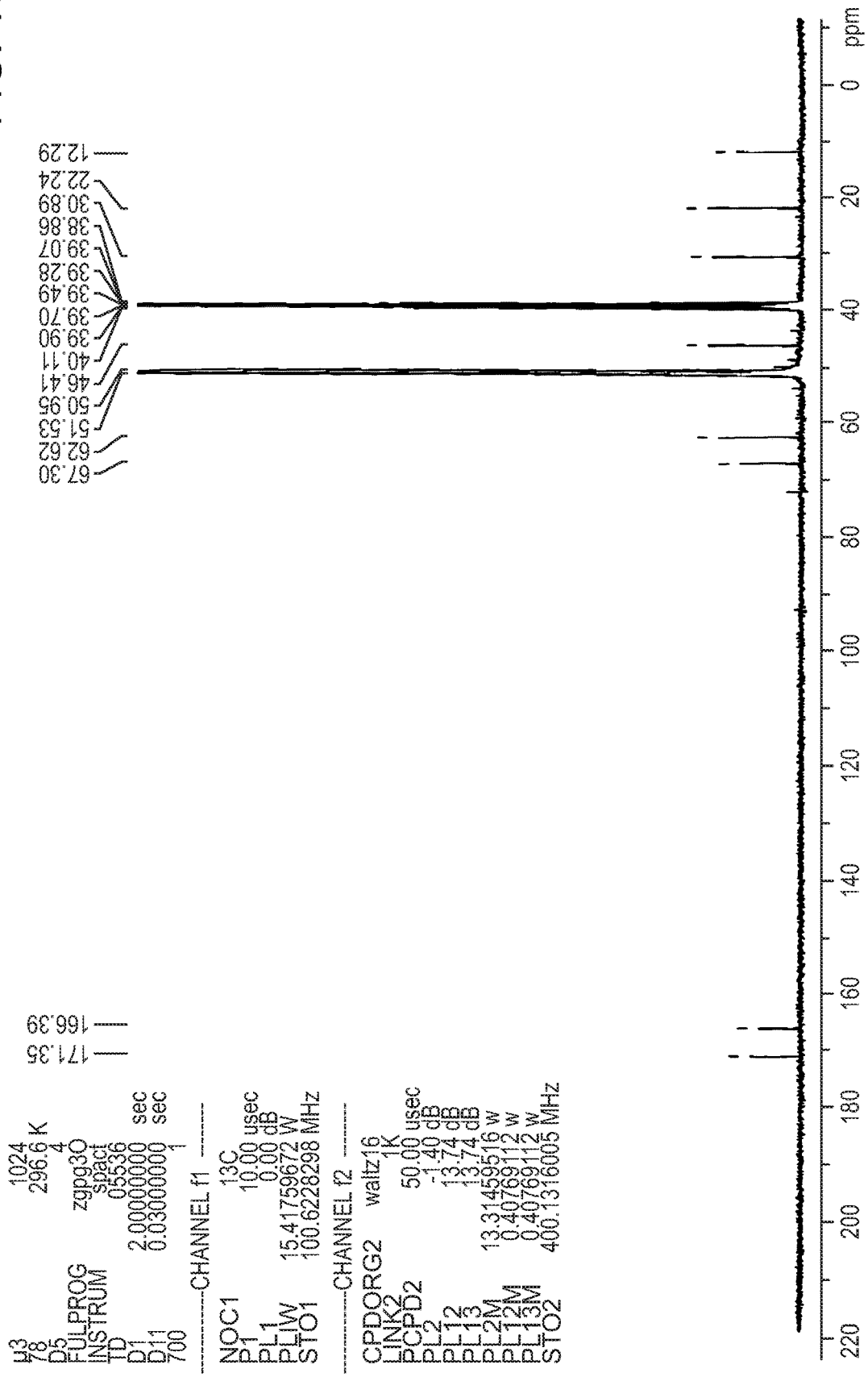
Figure 19A:
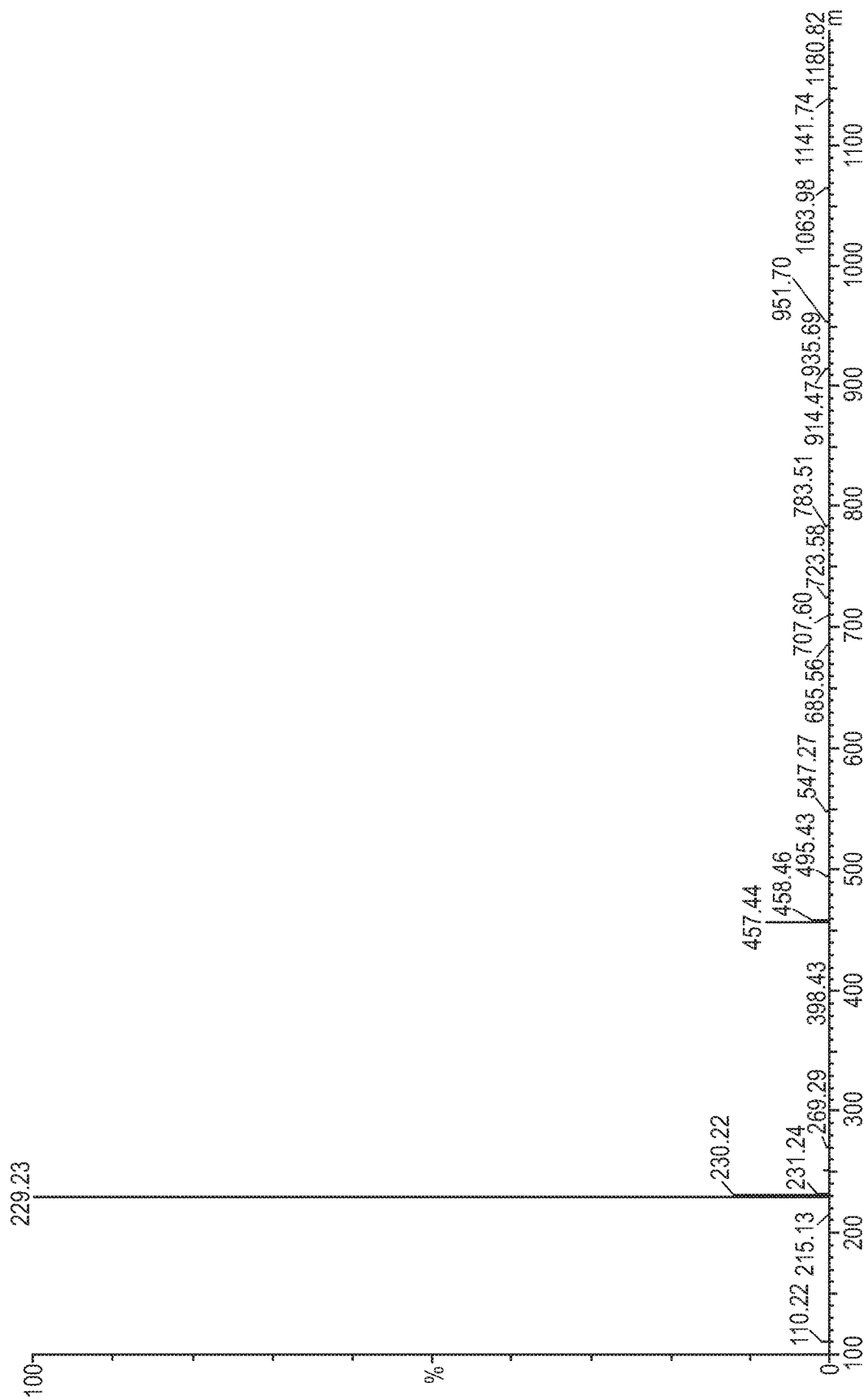
FIGS. 19A and 19B show mass spectra of the unlabeled TMAP (FIG. 19A) and $^{13}$C-labeled TMAP (FIG. 19B).
Figure 19B:
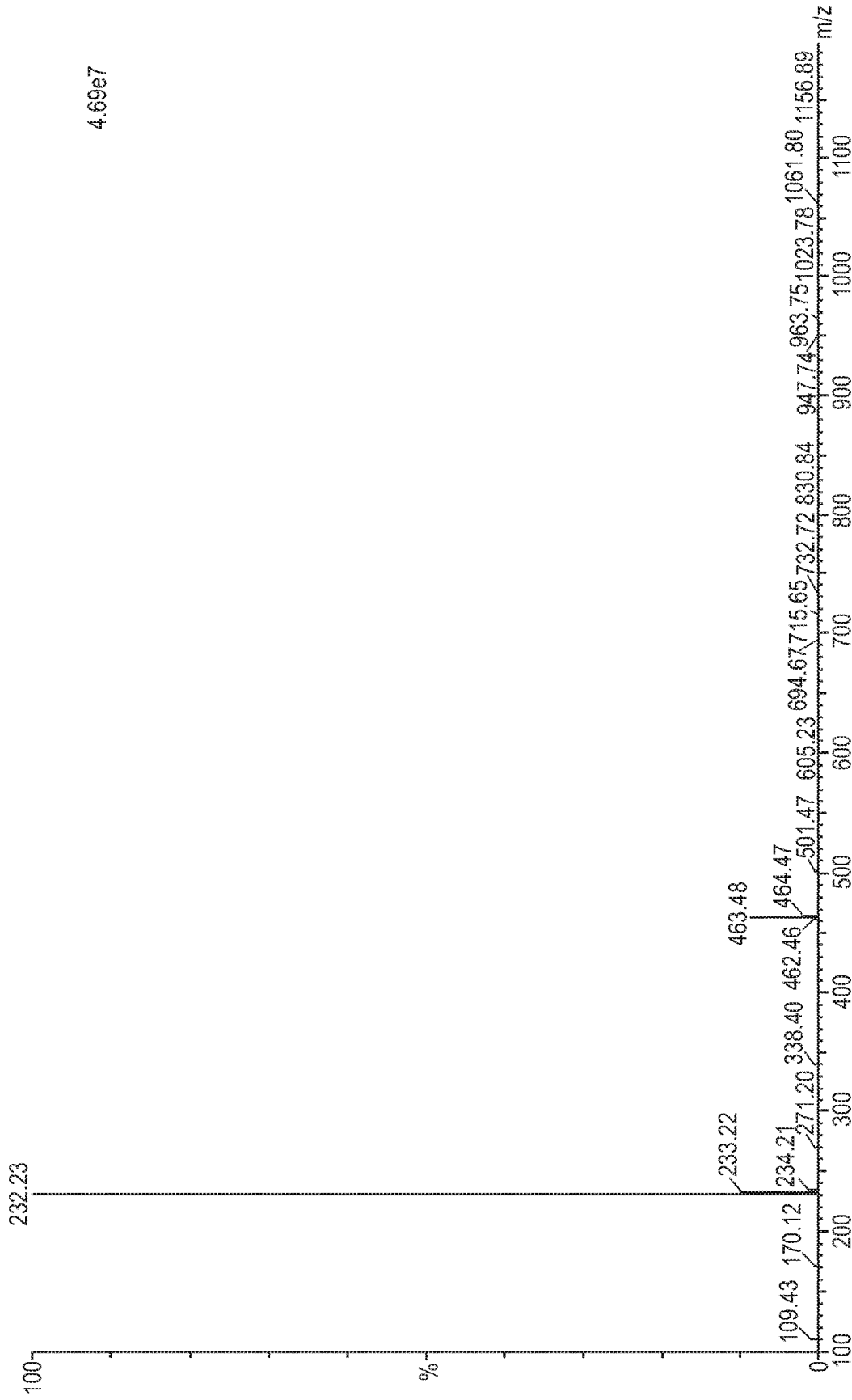

FIGS. 18A and 18B show $^{13}C$-NMR spectra of the $^{13}C$-labeled TMAP ($^{13}C_3$-L,L-TMAP) as compared to the unlabeled TMAP. FIGS. 19A and 19B show mass spectra of the $^{13}C$-labeled TMAP ($^{13}C_3$-L,L-TMAP) as compared to the unlabeled TMAP.

Method 2. In a 4 mL glass vial with a magnetic stir bar were added L-alanyl-L-proline (20.0 mg, 0.108 mmol), potassium carbonate (50.0 mg, 0.362 mmol), and 1.0 mL of methanol/water (4:1). The solution mixture was stirred on a magnetic stirrer at room temperature and 75 µL of iodomethane (171 mg, 1.2 mmol) added. The vial was loosely capped and the mixture stirred overnight at room temperature in dark. The resulting mixture was evaporated to dryness under a gentle stream of nitrogen at 40° C. The residue was dissolved in 1.0 mL of water. The solution was diluted 10,000 fold with 0.1% formic acid in water and transferred to a sample vial for LC/MS analysis.

Method 3. A general strategy for a third synthetic approach is represented below. A dipeptide with the carboxyl group protected may be used as the starting molecule. Any suitable carboxyl protecting group can be used (T. W. Green, P. G. M. Wuts, *Protective Groups in Organic Synthesis*, Wiley-Interscience, New York, 1999). In one embodiment, the protecting group X may be an alkyl group, such as methyl, ethyl, tert-butyl, or benzyl groups. In another embodiment, the protecting group is a silyl group, such as triakylsilyl group (e.g. trimethylsilyl). The removal of the protecting group X depends on the nature of the protecting group X. In one embodiment, the protecting group can be removed by the treatment with an acid.

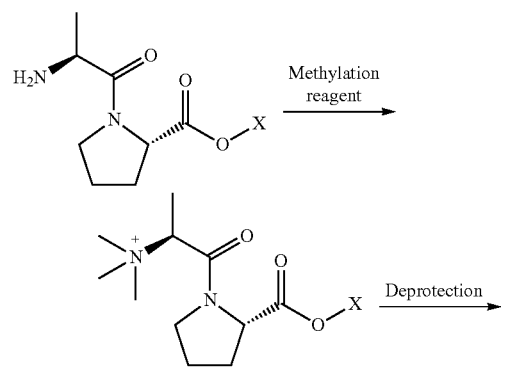

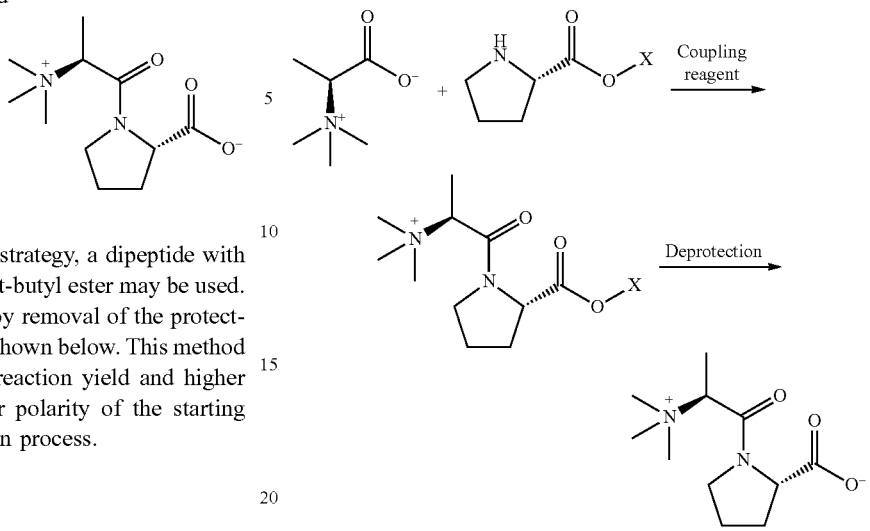

In one example of this general strategy, a dipeptide with the carboxyl group protected by a t-butyl ester may be used. A methylation reaction followed by removal of the protecting group will generate TMAP as shown below. This method may be advantageous for better reaction yield and higher product purity because the lower polarity of the starting material may facilitate the reaction process.

In one example of this general strategy, a N,N,N-trimethyl-L-alanine and a L-proline with the carboxyl group protected by a t-butyl ester may be used. The coupling of the N,N,N-trimethyl-L-alanine and the carboxyl group protected L-proline, may be accomplished by EDC or any other suitable activating agnet described above. The removal of the protecting group will generate TMAP.

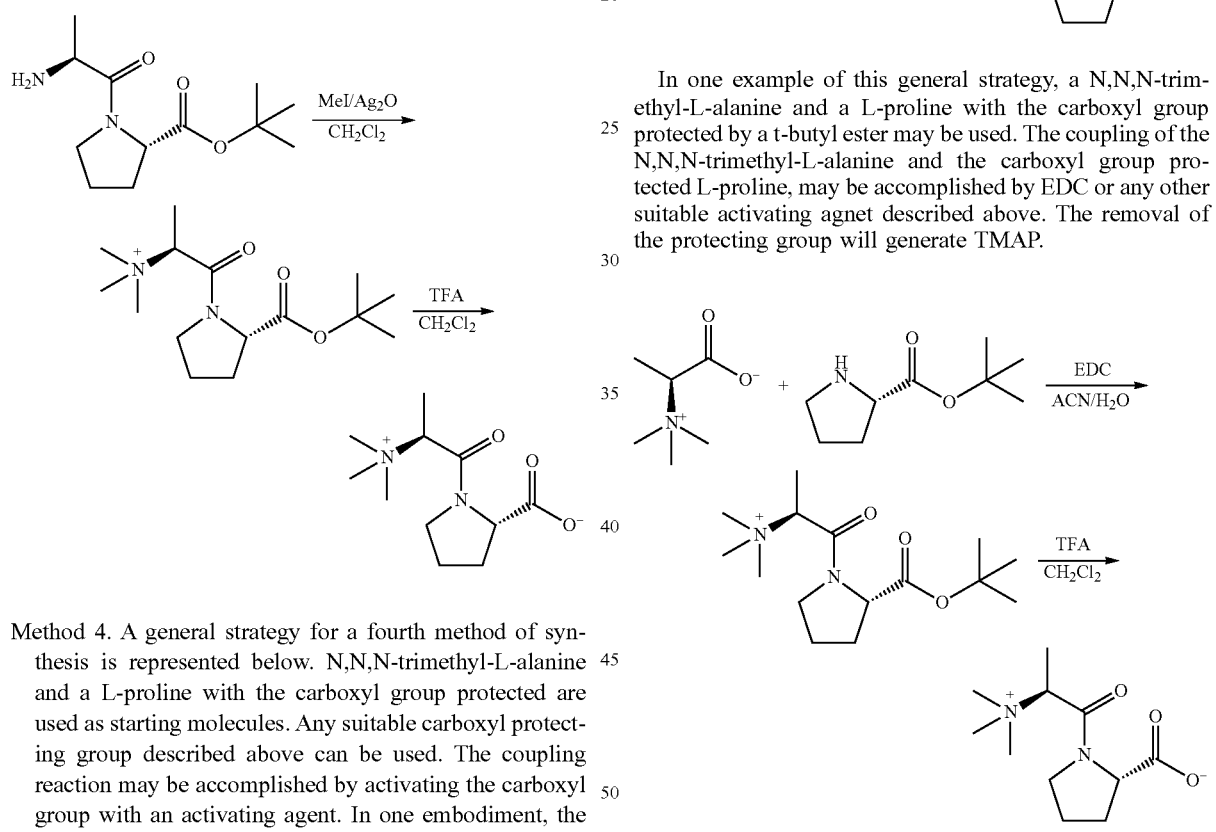

Method 4. A general strategy for a fourth method of synthesis is represented below. N,N,N-trimethyl-L-alanine and a L-proline with the carboxyl group protected are used as starting molecules. Any suitable carboxyl protecting group described above can be used. The coupling reaction may be accomplished by activating the carboxyl group with an activating agent. In one embodiment, the activating agent is a carbodiimide, a uronium, an active ester, a phosphonium, 2-alkyl-1-alkylcarbonyl-1,2-dihydroquinoline, 2-alkoxy-1-alkoxycarbonyl-1,2-dihydroquinoline, or alkylchloroformate. In a specific embodiment, the activating agent is a carbodiimide, such as dicyclohexylcarbodiimide (DCC), 1-ethyl-3-(3-dimethylaminopropyl)carbodiimide (EDC), or diisopropylcarbodiimide (DIC). In another embodiment, the carboxyl group can be activated by formation of acyl halide using, for example, $SOCl_2$, oxalyl chloride, or other suitable reagents. The removal of the protecting group X depends on the nature of the protecting group X. In one embodiment, the protecting group is removed by the treatment with an acid.

Method 5. In another example, the starting material may be N-methyl-L-alanyl-L-proline ($R_1$=H and $R_2$=$CH_3$) or N,N-dimethyl-L-alanyl-L-proline ($R_1$=$R_2$=$CH_3$), and the reaction conditions described in Method 1 may be used.

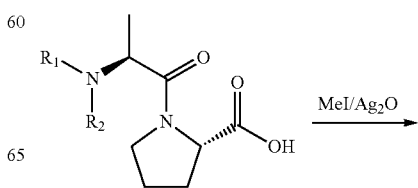

-continued

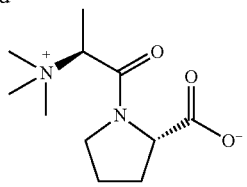

Example 2

Structure Elucidation of Plasma Metabolite Compound A

Sample Preparation

In a 1.5 mL Eppendorf tube were added 100 μL of human plasma (thawed on ice) and 500 μL of methanol. The mixture was vortexed for 2 min and centrifuged at room temperature for 5 min at 14,000 rpm. The supernatant was transferred to a new tube and dried under a gentle stream of nitrogen at 40° C. To the residue was added 200 μL of water with 0.1% formic acid, and the mixture was vortexed for 1 min and centrifuged at room temperature for 10 min at 14,000 rpm. The supernatant was then transferred to a sample vial for LC/MS analysis.

Structure Elucidation

Figure 2:
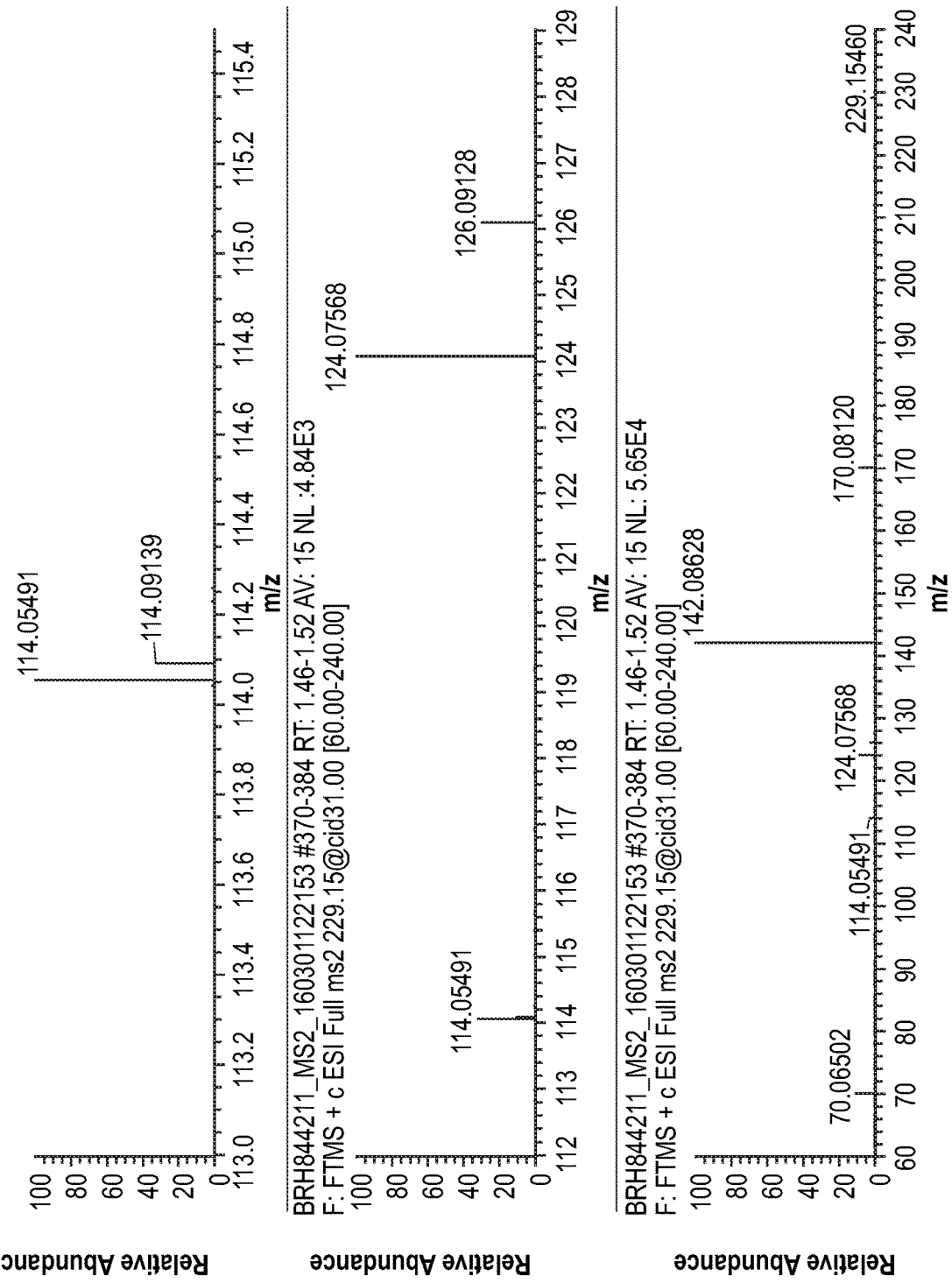
FIG. 2 shows product ion spectrum ($MS^2$) of compound A in plasma sample with expansions.
Figure 3:
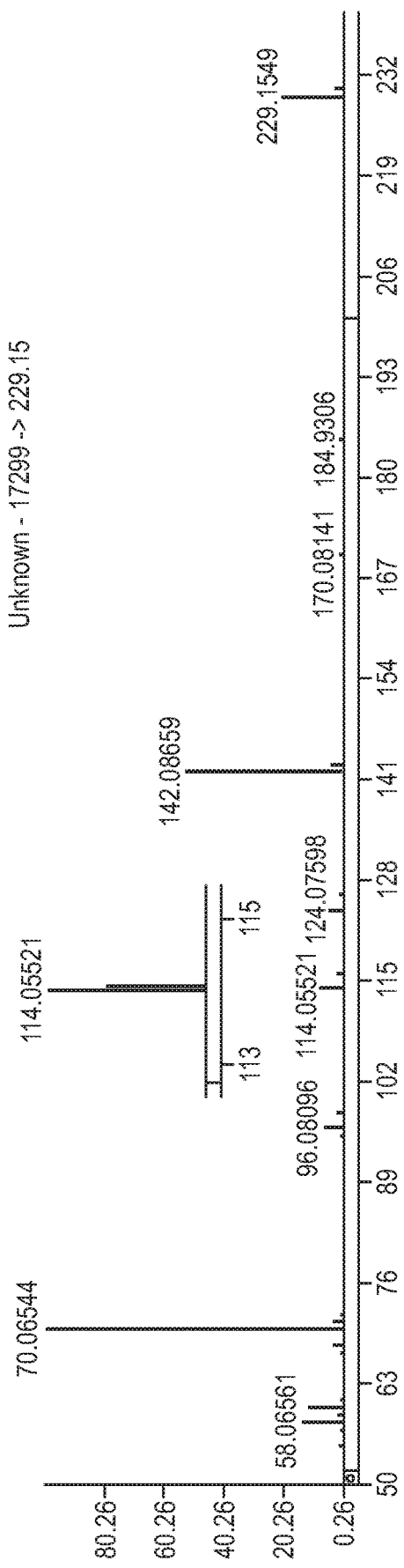
FIG. 3 shows product ion spectrum ($MS^2$) of compound A in plasma sample collected on a Q-Exactive mass spectrometer.
Figure 4:
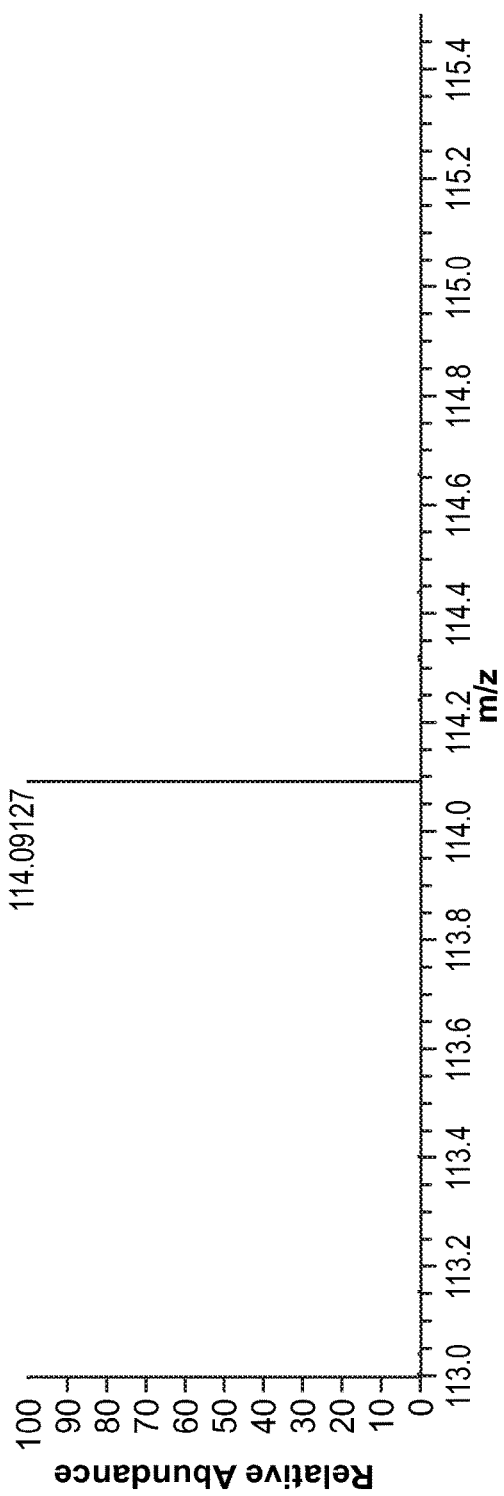
FIG. 4 shows $MS^3$ spectrum of m/z 142 of compound A.
Figure 4:
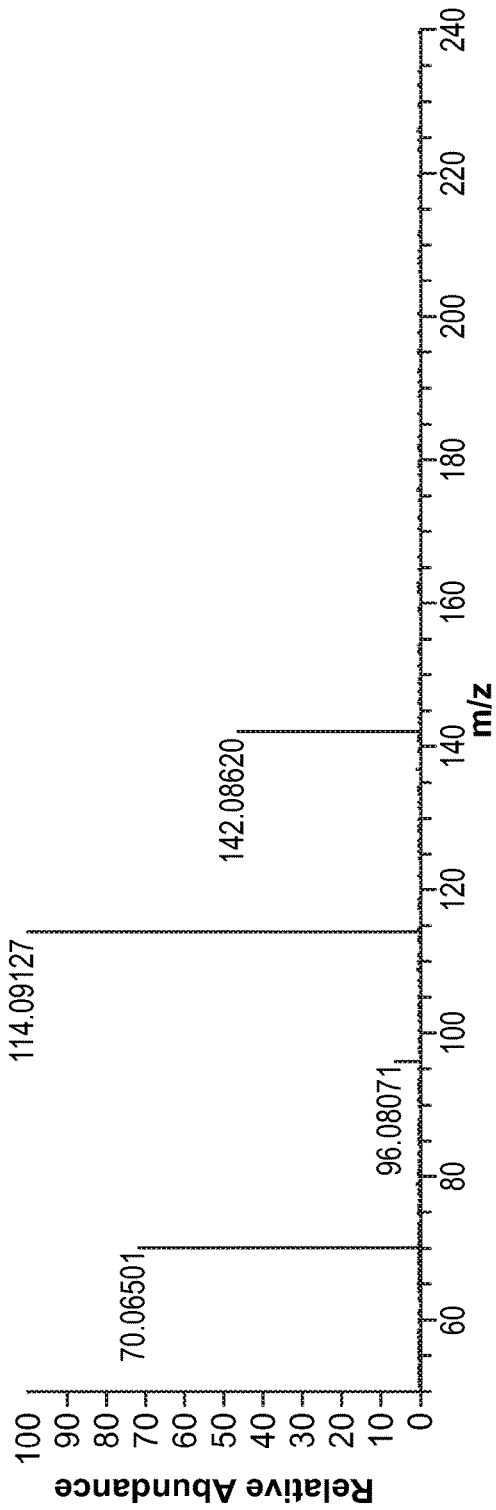
Figure 5:
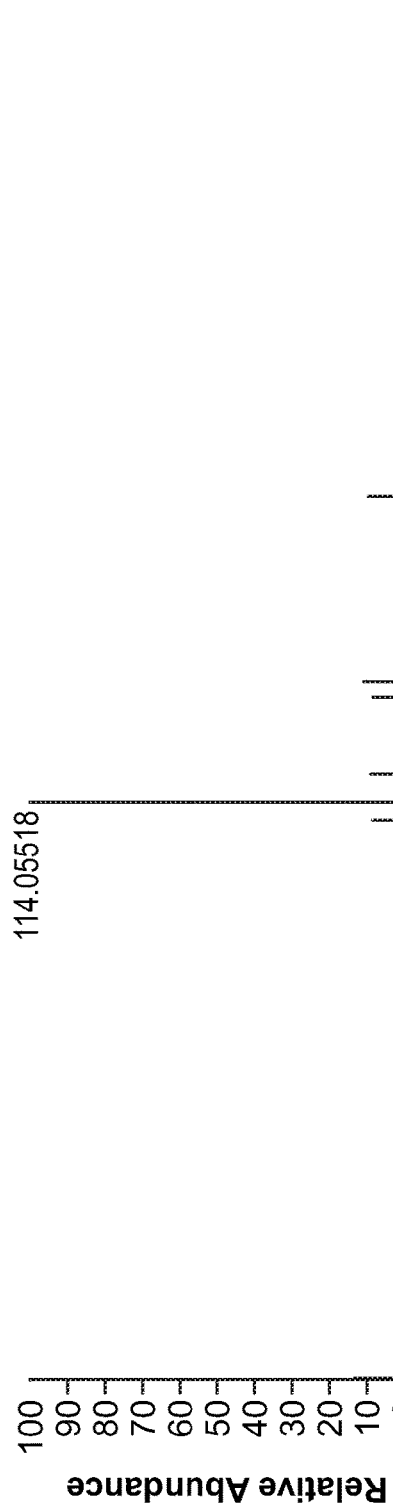
FIG. 5 shows $MS^3$ spectrum of m/z 170 of compound A.
Figure 5:
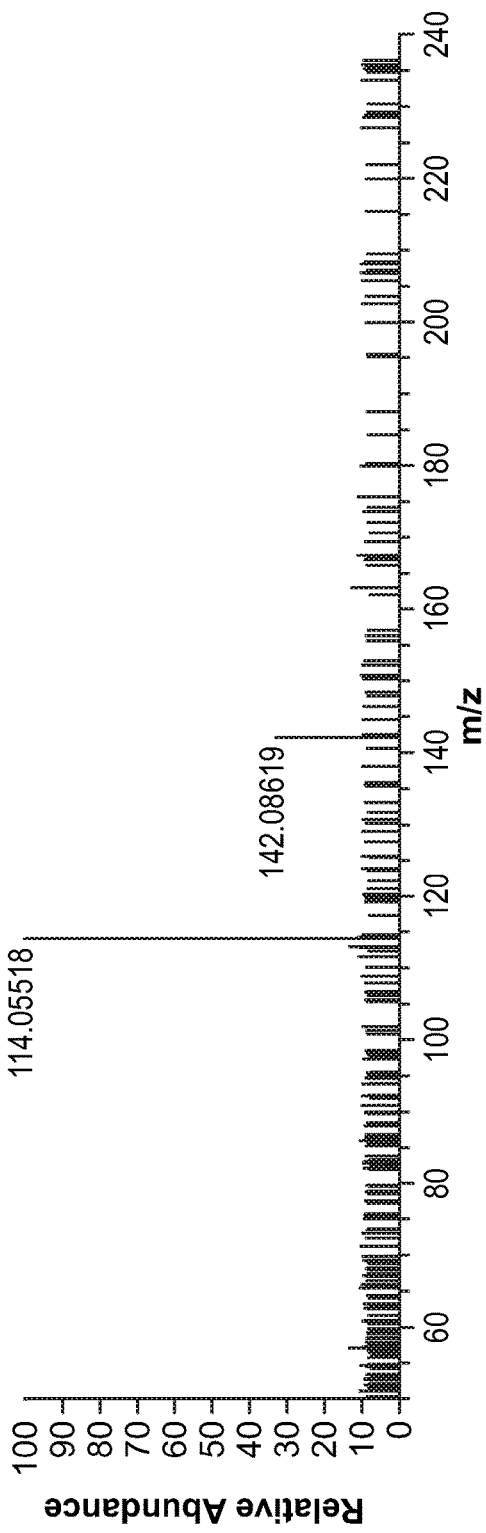
Figure 6:
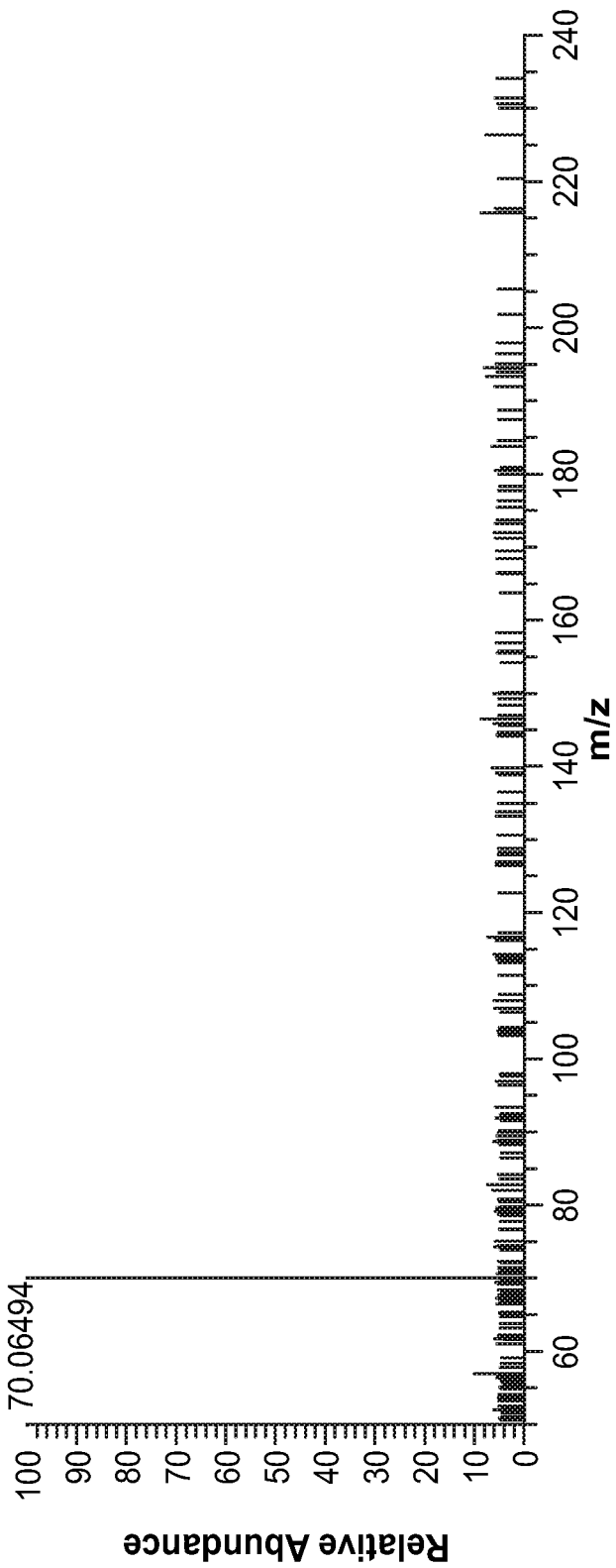
FIG. 6 shows $MS^4$ spectrum of m/z 114.09 of compound A.

An Orbitrap Elite mass spectrometer was used for acquisition of high resolution mass spectra. The formula of the protonated pseudo molecular ion was previously determined to be $C_{11}H_{21}O_3N_2^+$ by accurate mass measurement. The current study started by optimizing the chromatography conditions to achieve longer retention for the metabolite compound A (1.48 min) without much emphasis on its peak shape as shown in the extracted ion chromatogram (FIG. 1). Collision induced dissociation (CID) of the pseudo molecular ion produced seven daughter ions as shown in FIG. 2, which are m/z 170, 142, 126, 124, 114.09, 114.05, and 70 (all collected with accurate mass, but omitted for simplicity hereafter). A product ion spectrum ($MS^2$) of the metabolite previously collected on a Q-Exactive mass spectrometer showed two additional daughter ions of m/z 96 and 58 (FIG. 3). Further fragmentation ($MS^3$, FIG. 4) of the predominant ion m/z 142 generated m/z 70, 114.09, and the m/z 96 ion, which was not detected in the Orbitrap CID $MS^2$ spectrum. The m/z 114.05 ion was not detected from the fragmentation of m/z 142, but instead it was formed by fragmentation of m/z 170 ($MS^3$, FIG. 5). The m/z 70 ion was detected when m/z 114.09 was further fragmented ($MS^4$, FIG. 6).

Rationalization of these fragments and their formation pathways allowed the proposal of a chemical structure for compound A as shown below:

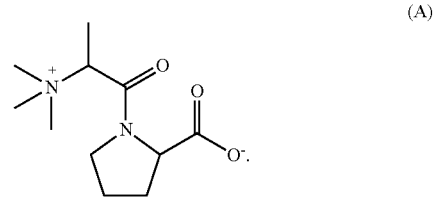

(A)

Stereochemistry analysis was performed on compound A, and the formula was determined to be represented by the following structure:

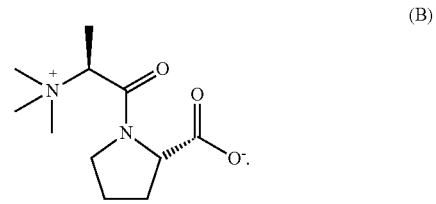

(B)

A possible fragmentation pathway from the protonated pseudo molecular ion of compound A is proposed as shown in Scheme 1.

Scheme 1.
Possible fragmentation pathway

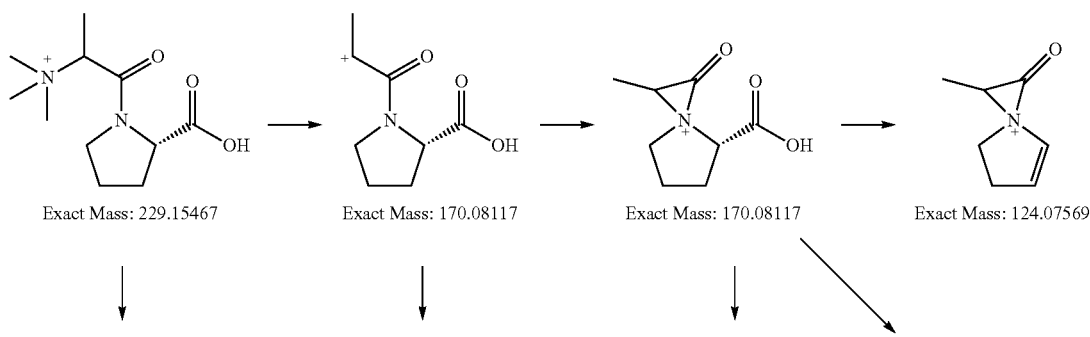

-continued

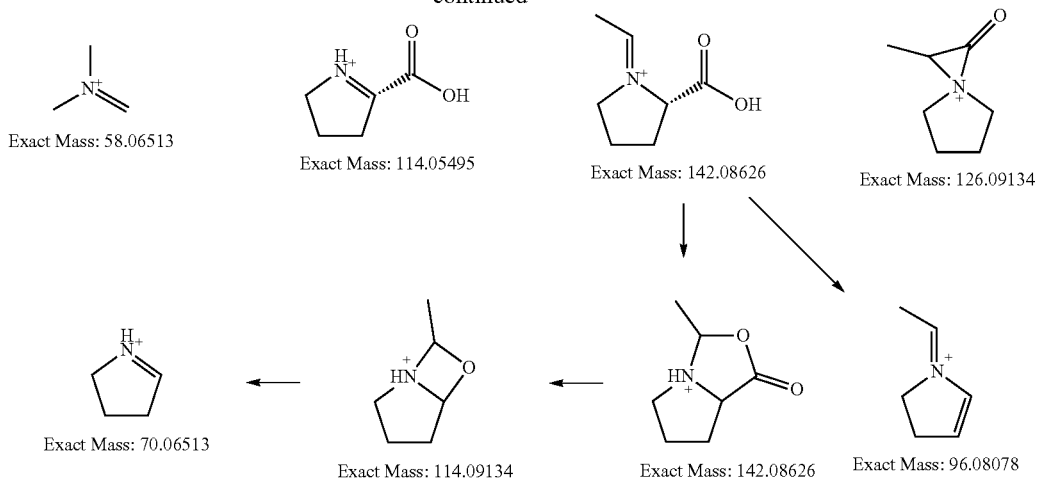

Structure Verification by Deuterium Exchange

Figure 7:
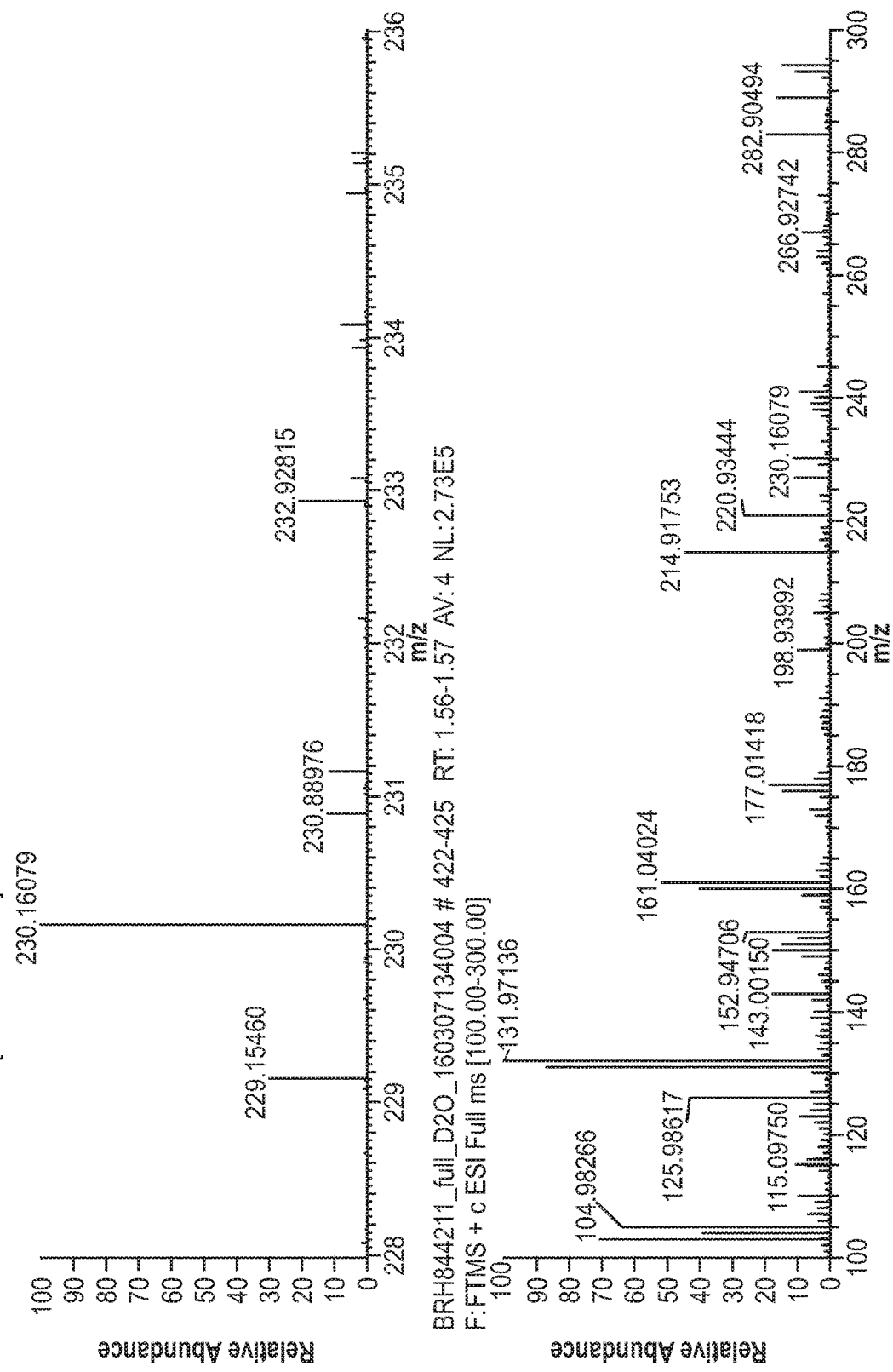
FIG. 7 shows full scan MS spectrum of deuterium exchanged compound A.
Figure 8:
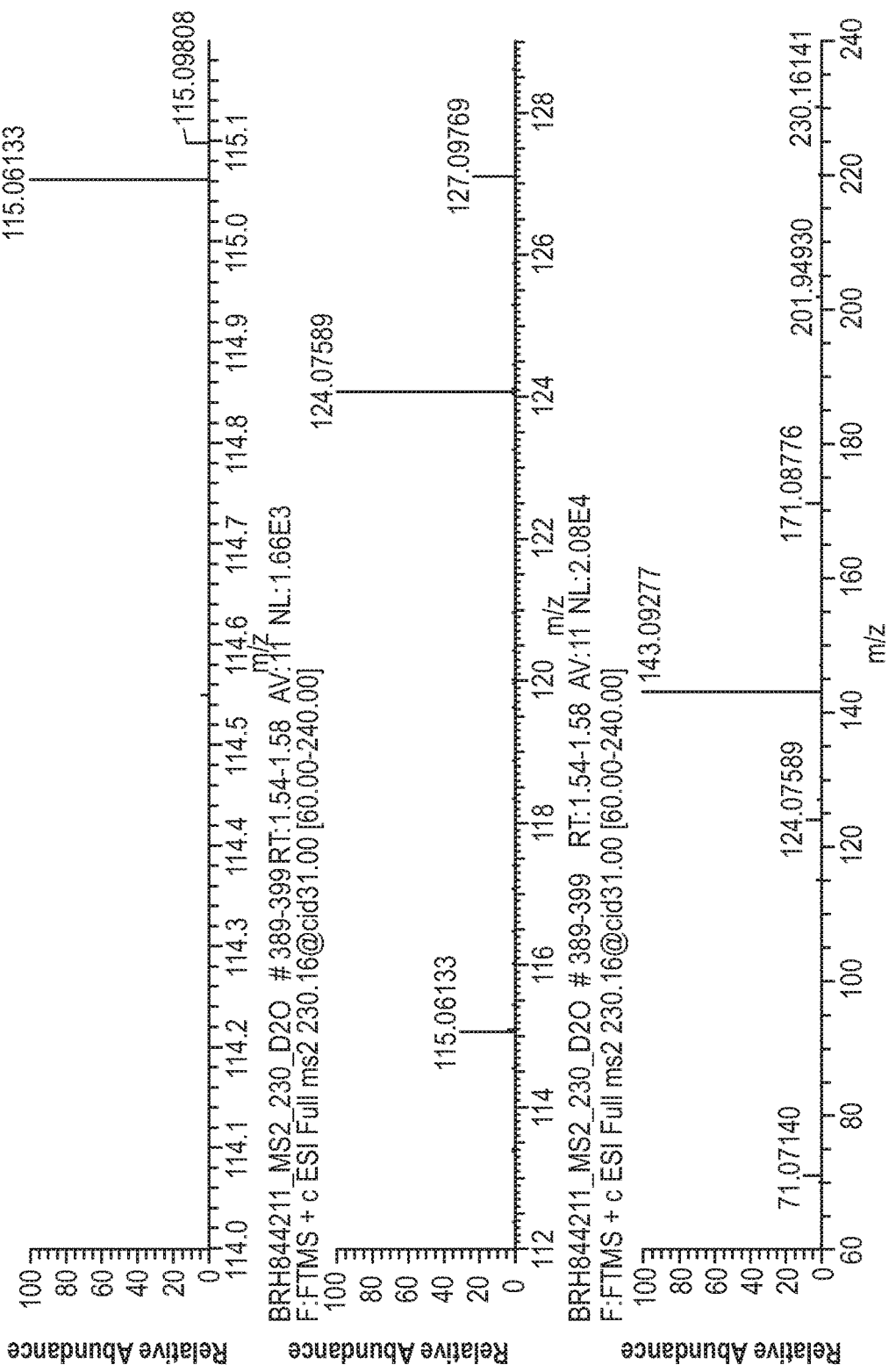
FIG. 8 shows $MS^2$ spectrum of deuterium exchanged compound A.
Figure 9:
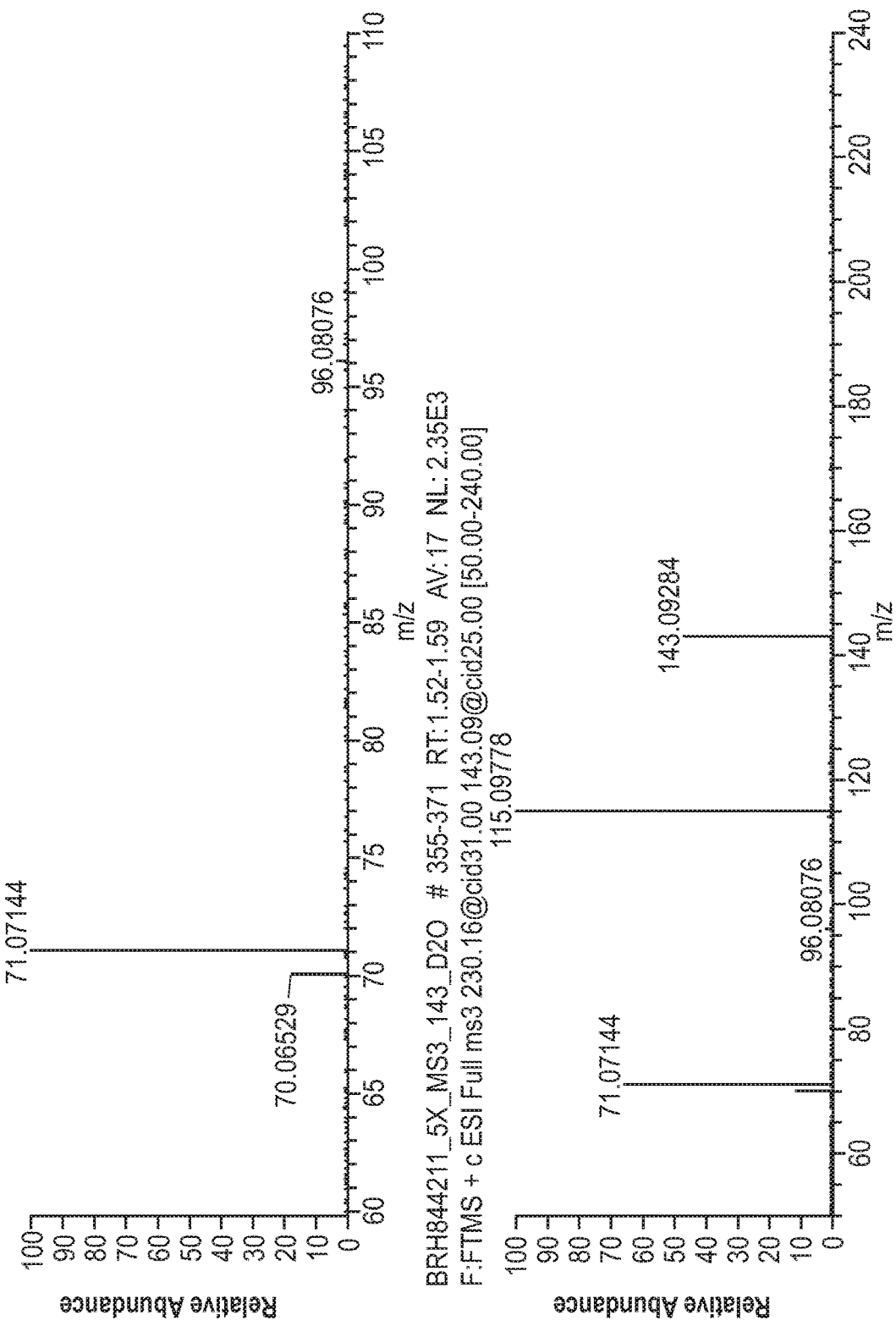
FIG. 9 shows $MS^3$ spectrum of m/z 143 deuterium exchanged compound A.

The proposed structure for compound A was first verified by a deuterium exchange experiment. Briefly, the mobile phase of chromatography was changed to deuterated solvent and the plasma extract was analyzed again. Full scan mass spectrum was acquired and a new m/z 230.16079 ion (−0.7 ppm off the calculated value of $C_{11}H_{20}DN_2O_3^+$) detected as the major species for deuterated compound A (FIG. 7), consistent with a single exchangeable proton of the proposed structure. Product ion spectrum ($MS^2$) of the m/z 230 ion and an $MS^3$ spectrum of the corresponding m/z 143 ion are shown in FIGS. 8 and 9. The corresponding deuterated fragments were detected at 171, 143, 127, 115.09, 115.06, and 71, while the fragments of 124 and 96 remained unchanged. All these ions can be satisfactorily rationalized into the originally proposed fragmentation pathway (see Scheme 2), providing convincing evidence for validity of the proposed structure of compound A.

Scheme 2.
Possible fragmentation pathway of deuterated analog.

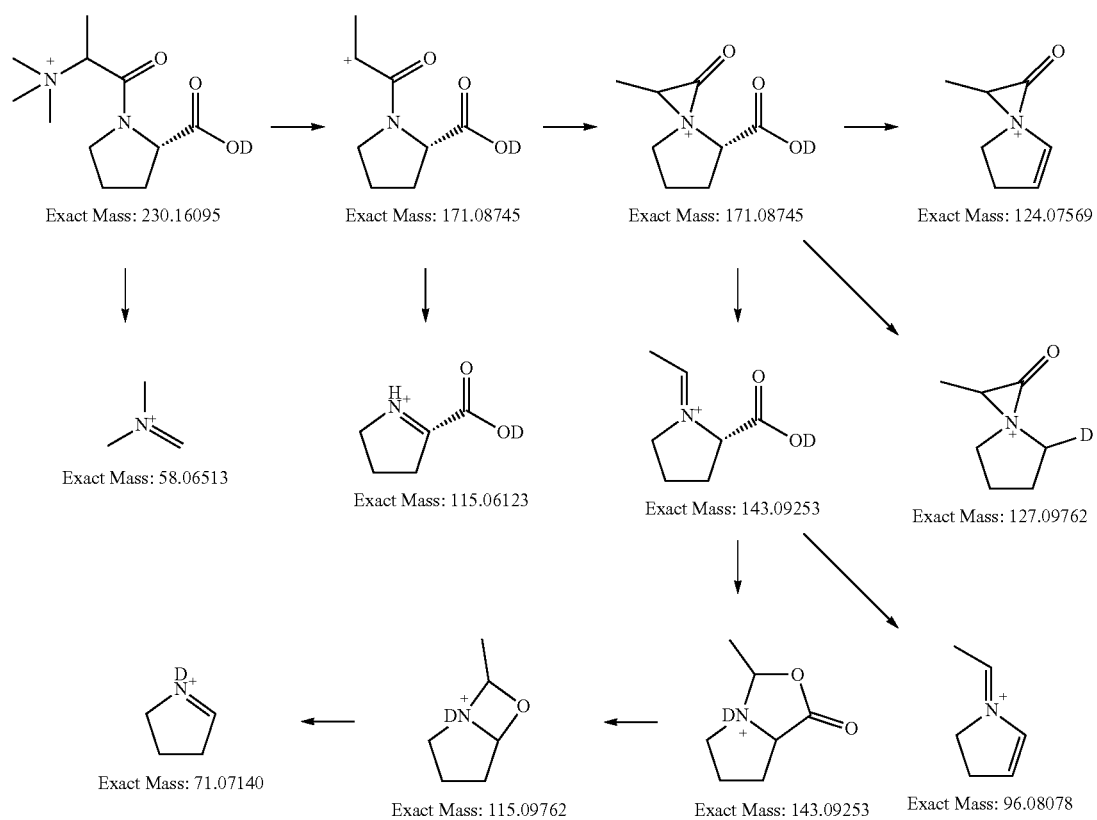

The proposed structure was further confirmed by direct comparison to a synthetic standard (see Example 1). Synthetic TMAP prepared by both method 1 and method 2 generated elutes at 1.44 minutes with a molecular ion of m/z 229.15415 (−2.3 ppm off calculated value) and 229.15403 (−2.8 ppm off calculated value) by LC/MS, respectively. The product prepared by method 1 was selected for further comparison to compound A.

Figure 10:
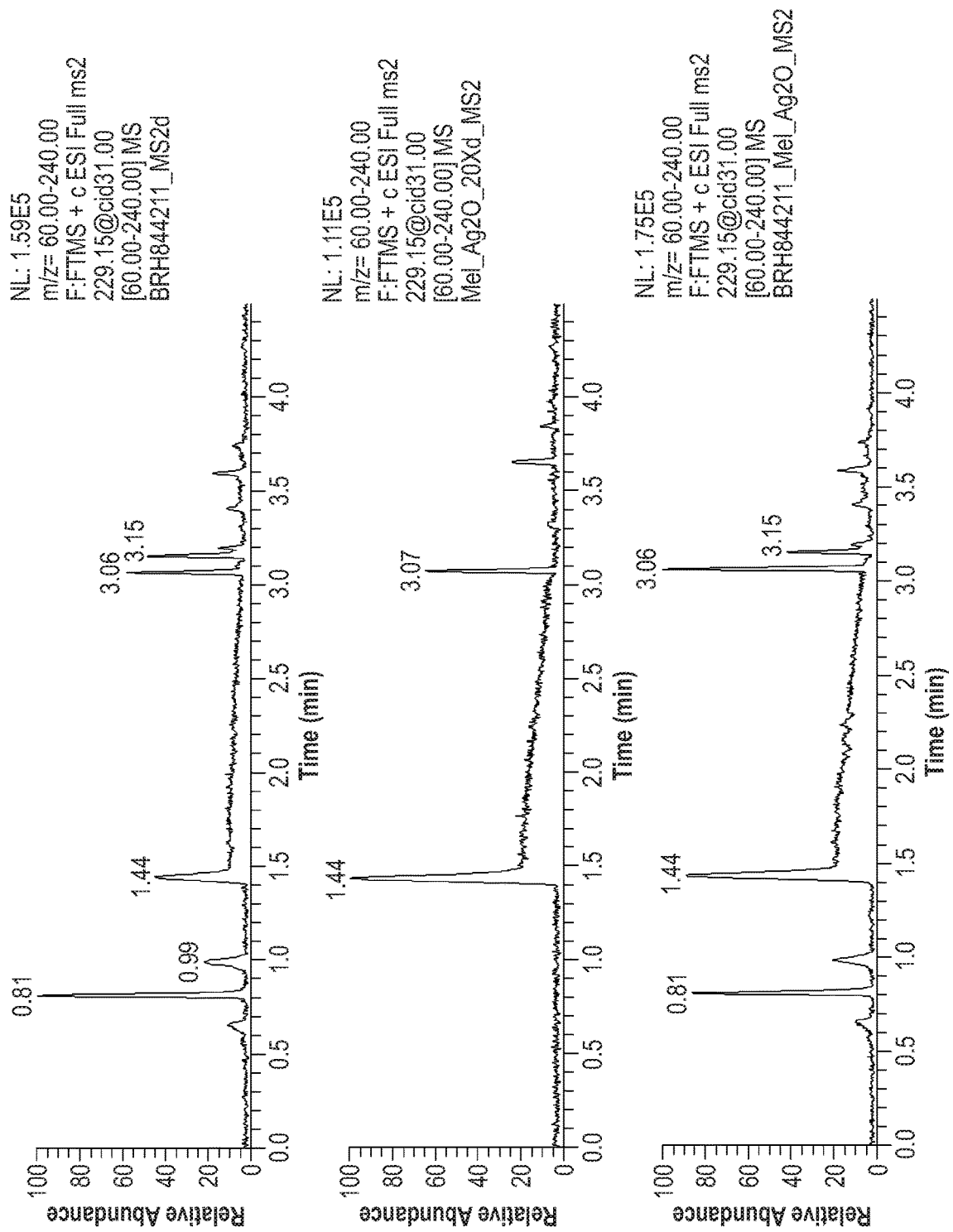
FIG. 10 shows LC-MS/MS chromatograms for compound A in plasma sample (top panel), synthetic TMAP (middle panel) and their co-injection (bottom panel).
Figure 11:
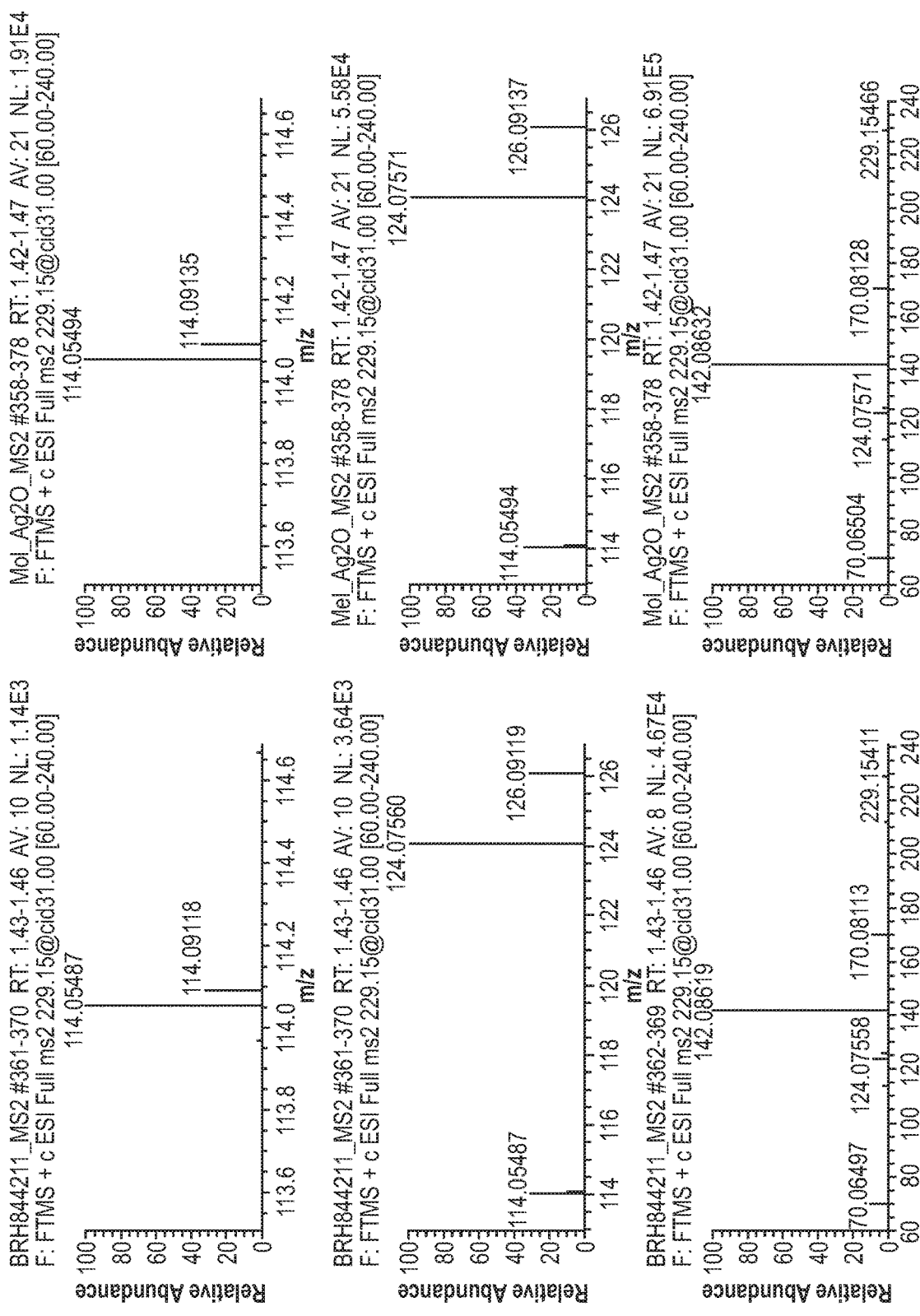
FIG. 11 shows $MS^2$ spectra for compound A in plasma sample (left panel) and synthetic TMAP (right panel).
Figure 12:
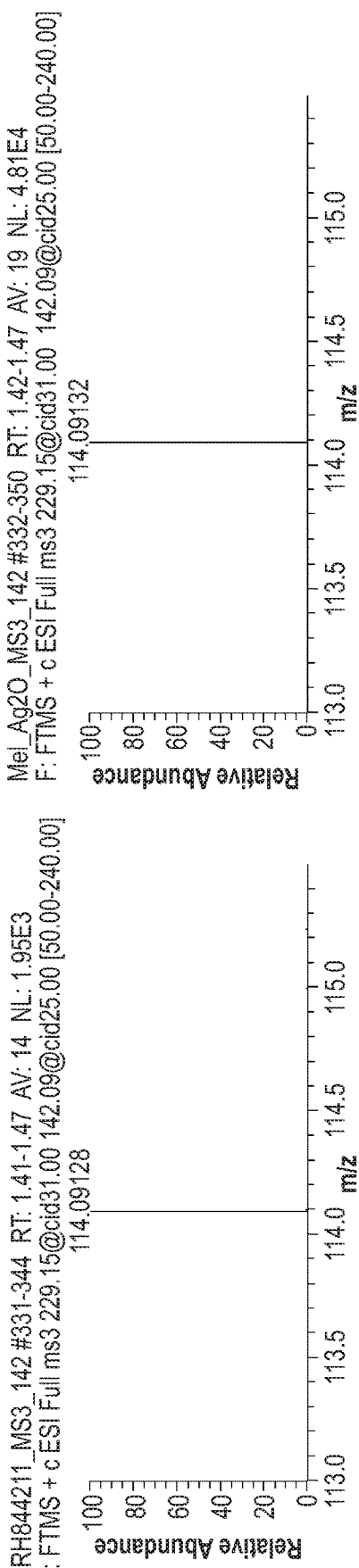
FIG. 12 shows $MS^3$ spectra of daughter ion m/z 142 for compound A in plasma sample (left panel) and synthetic TMAP (right panel).
Figure 13:
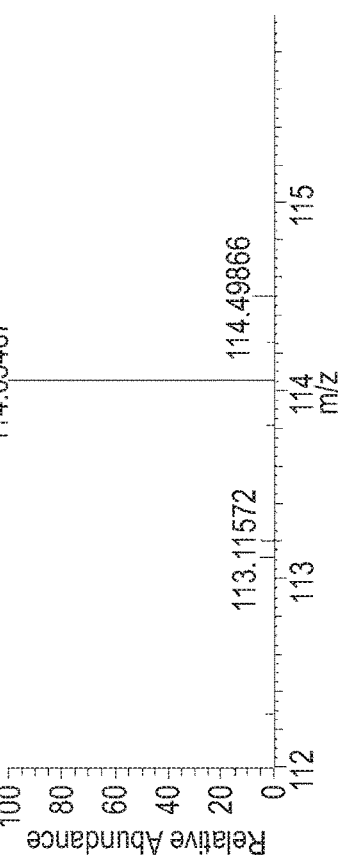
FIG. 13 shows $MS^3$ spectra of daughter ion m/z 170 for compound A in plasma sample (left panels) and synthetic TMAP (right panels).
Figure 13:
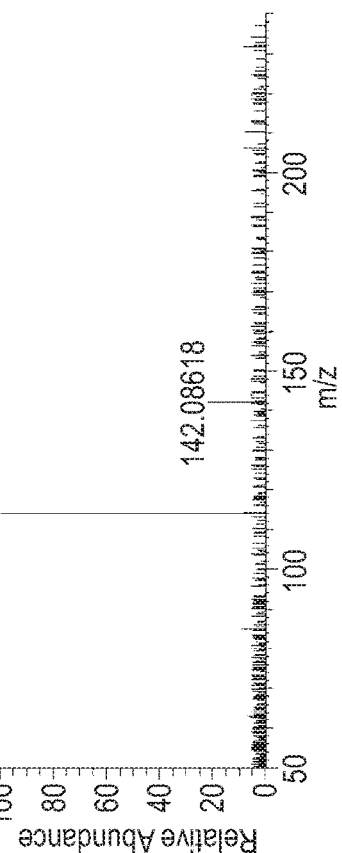
Figure 13:
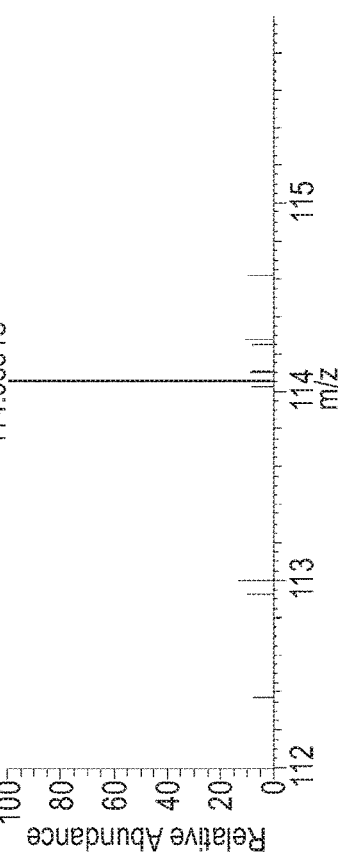
Figure 13:
Figure 14:
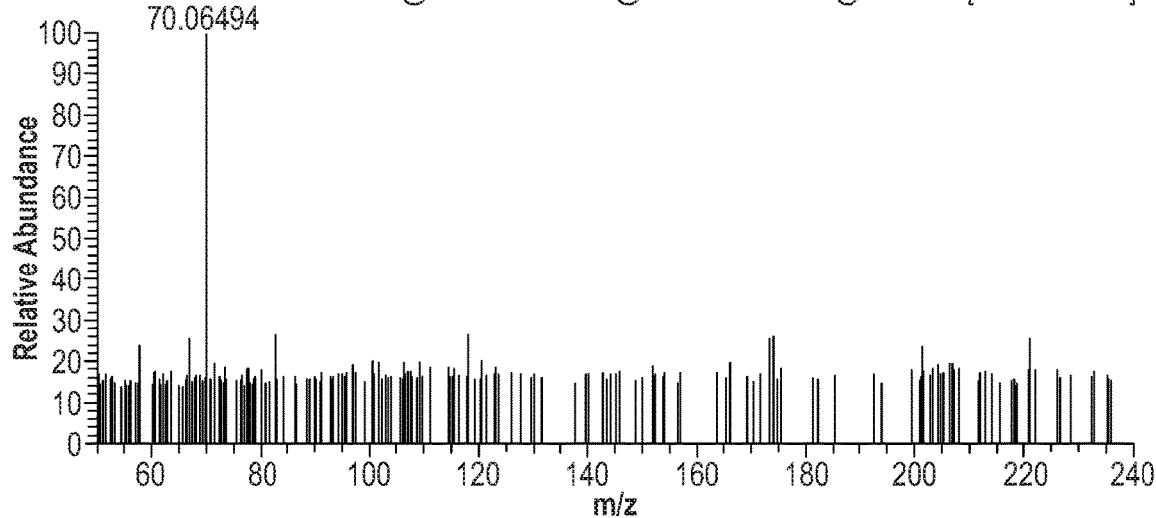
FIG. 14 shows $MS^4$ spectra of daughter ion m/z 114.09 for compound A in plasma sample (top panel) and synthetic TMAP (bottom panel).
Figure 14:
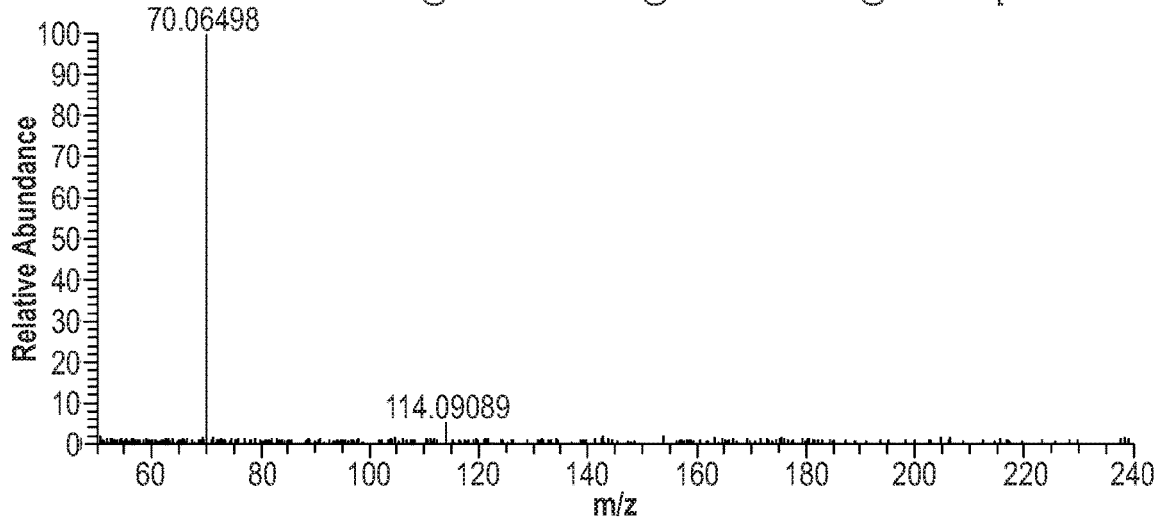
Figure 15:
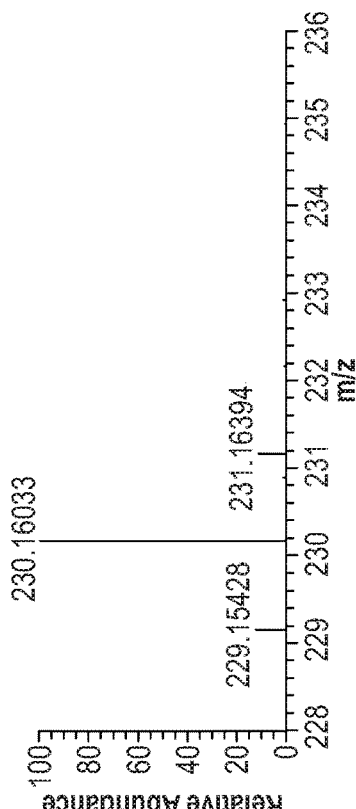
FIG. 15 shows deuterium exchanged full scan MS spectra of compound A in plasma sample (left panel) and synthetic TMAP (right panel).
Figure 15:
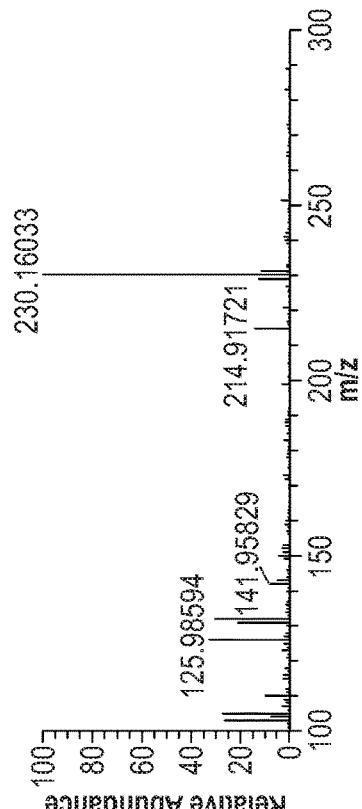
Figure 15:
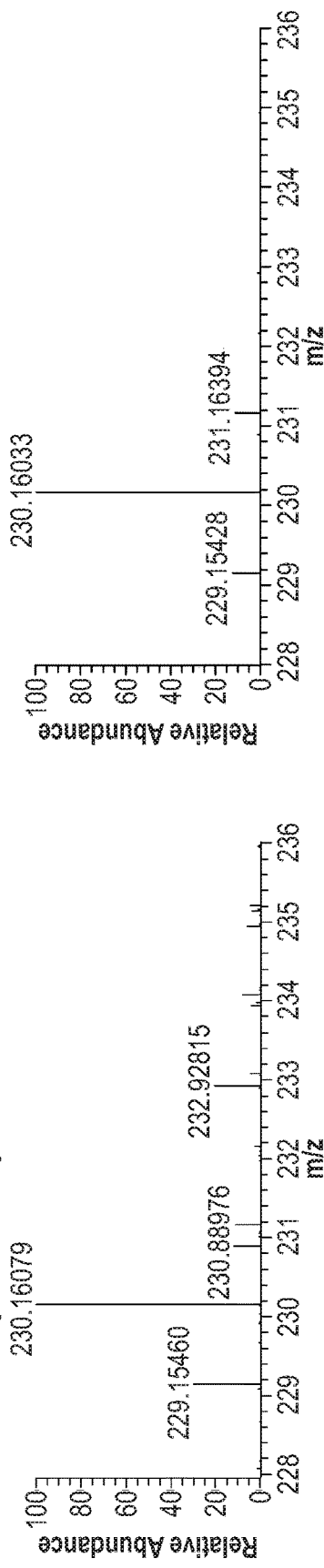
Figure 15:
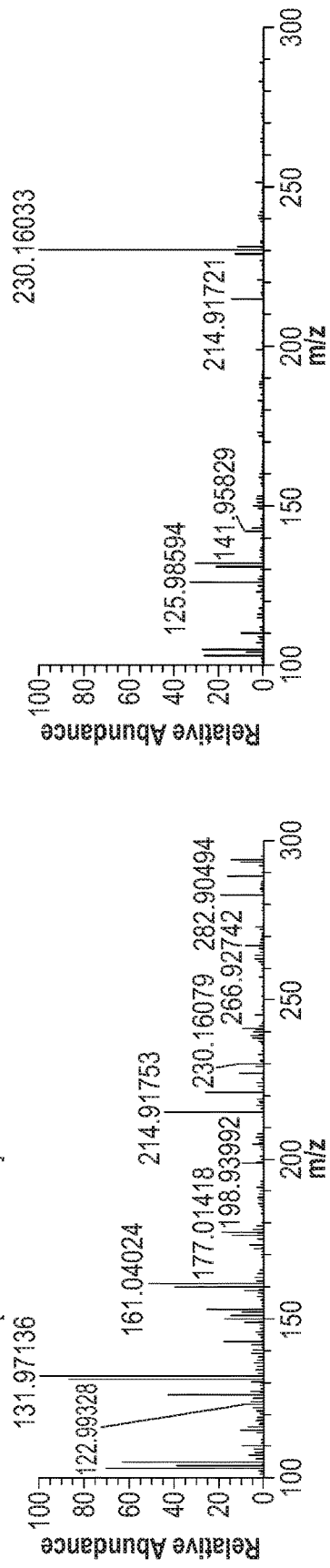
Figure 16:
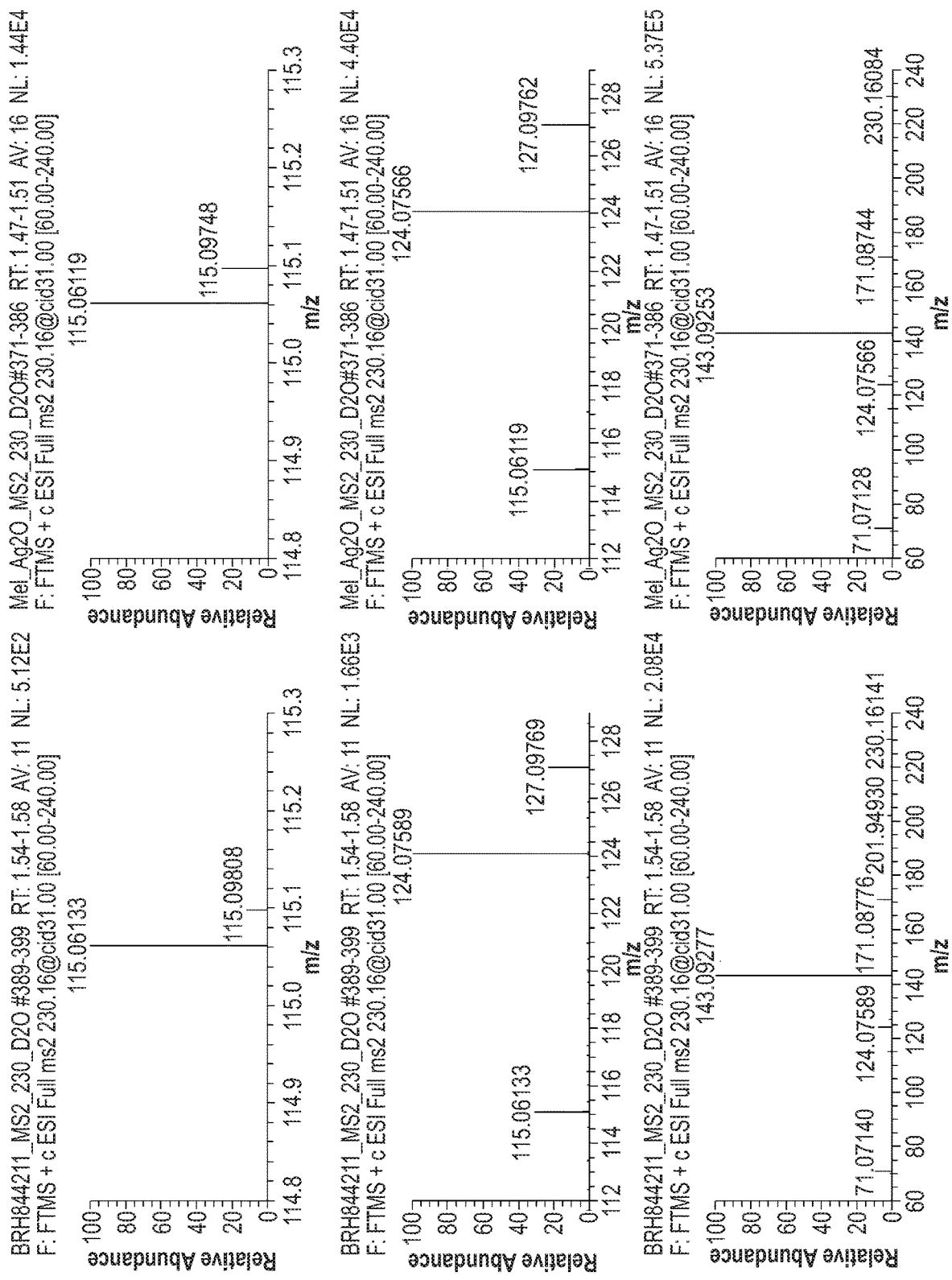
FIG. 16 shows deuterium exchanged $MS^2$ spectra of compound A in plasma sample (left panel) and synthetic TMAP (right panel)
Figure 17:
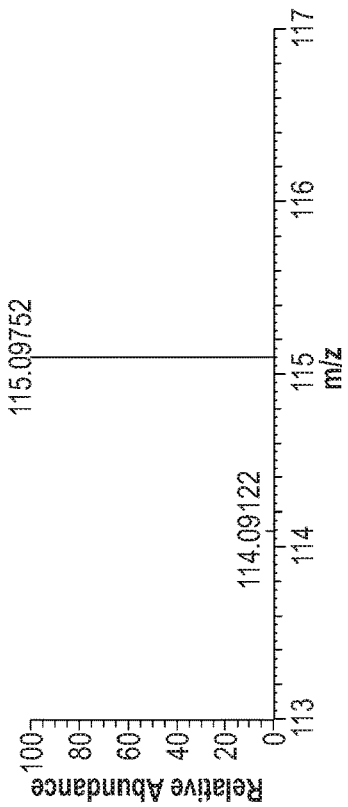
FIG. 17 shows deuterium exchanged $MS^3$ spectra of m/z 143 for compound A (left) and synthetic TMAP (right)
Figure 17:
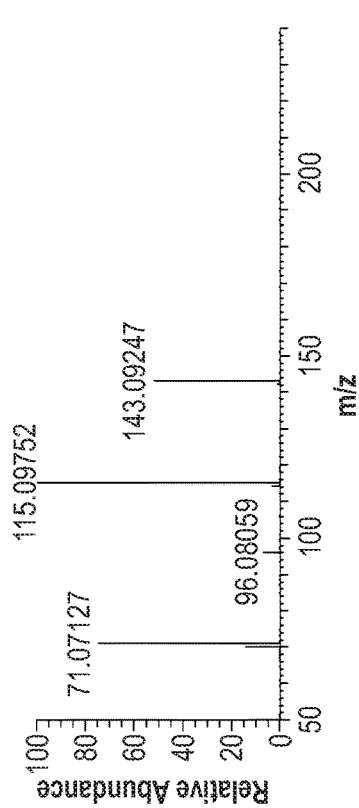
Figure 17:
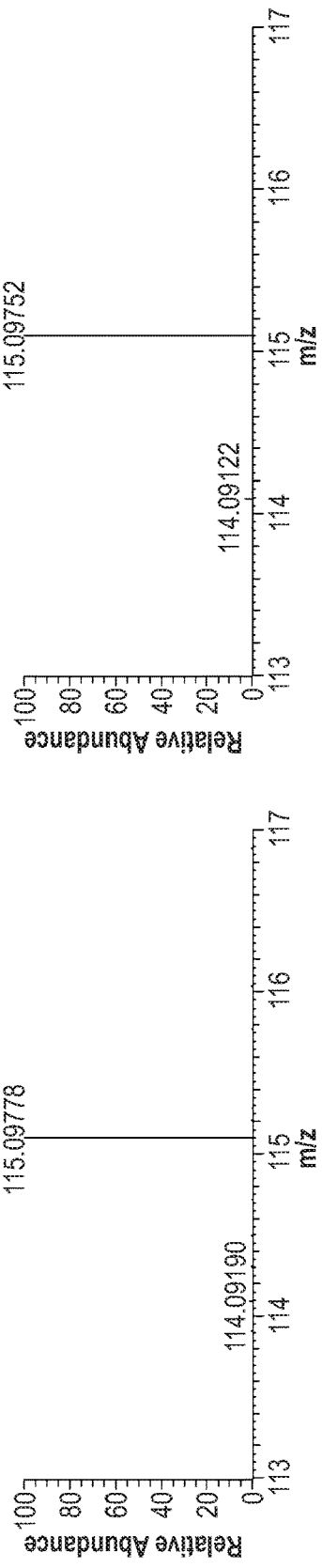
Figure 17:
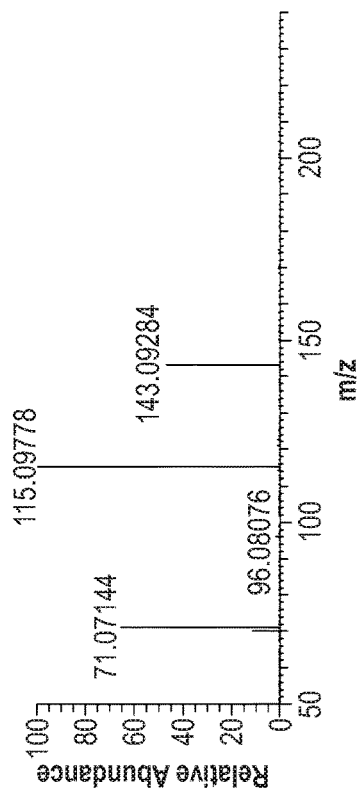

The retention time of the synthetic TMAP (middle panel in FIG. 10) perfectly matched that of compound A (top panel) as they co-eluted (bottom panel) under the chromatographic conditions. As an unexpected bonus, the characteristic peak tailing of the synthetic TMAP also resembled that of compound A. Product ion spectrum ($MS^2$) of synthetic TMAP agreed remarkably well with that of compound A by fragments and their relative intensity (FIG. 11). Further fragmentation of the 142 and 170 daughter ions of synthetic TMAP produced $MS^3$ spectra, which were essentially identical to those from compound A as compared side by side in FIGS. 12 and 13, respectively. An $MS^4$ spectrum of the synthetic TMAP on the m/z 114 ion showed a m/z 70 fragment, consistent with that of compound A (FIG. 14). Furthermore, the synthetic TMAP was analyzed after deuterium exchange and the resulting MS, $MS^2$, and $MS^3$ spectra also matched those of compound A very well as shown in FIGS. 15-17. All these chromatographic and MS spectral data strongly support that compound A is TMAP.

Example 3

Compound A as A Biomarker for Kidney Function

An extensive study was carried out by analyzing a large number of plasma and serum samples from healthy and diseased individuals (see WO 2014/186311). The results show that the serum level of compound A correlates with glomerular filtration rate (GFR) with statistic significance (see, for examples, Tables 1, 2 and 4 in WO 2014/186311), particularly in patient with intermediate eGFRs. For patients with intermediate eGFR, the assessment of kidney function and diagnosis of CKD is uncertain using traditional diagnostic methods.

TMAP correlation with CKD-EPIcr eGFR is −0.648 and the correlation with MDRDcr eGFR is −0.582. The correlation of serum creatinine with CKD-EPIcr eGFR is −0.673 and with MDRDcr eGFR is −0.632.

Example 4

LC-MS/MS Measurement of Compound A

Reversed phase liquid chromatography was performed to measure compound A. A Waters Acquity UPLC system equipped with a binary solvent manager, a refrigerated sample manager (set at 12° C.), and a column manager (set at 40° C.) were used for liquid chromatography with a reversed phase column (Waters ACQUITY UPLC® BEH C18, 1.7 µm, 2.1×100 mm). Mobile phase A was 0.1% formic acid in water, and mobile phase B was 0.1% formic acid in methanol. Linear gradient elution was carried out with an initial condition of 0% mobile phase B, which was held for 2.00 min. Mobile phase B was then increased to 98% in 0.50 min and maintained for 0.90 min. Mobile phase B reverted to 0% in 0.10 min for equilibration for the next injection. The flow rate was 350 µL/min and the total run time was 4.50 min. A loop fixed aliquot of 5.0 µL of the final sample solution was injected for each sample. The eluent was directly introduced into the electrospray source of a mass spectrometer. Strong needle wash was neat methanol and weak needle wash was a mixture of methanol and water (0.5:99.5). Seal wash was a mixture of methanol and water (10:90).

Mass spectrometry was performed using a Thermo Scientific Orbitrap Elite mass spectrometer equipped with a heated electrospray ionization (HESI-II) probe operated positive mode. The instrument was controlled by Orbitrap Elite™ 2.7 and XCalibur™ 2.2 software. The heated electrospray source was set with heater temperature at 430° C., sheath gas at 30, and auxiliary gas flow rates at 12, sweep gas at 0, ion spray voltage at 4.20 kV, capillary temperature at 350° C., and S-lens RF level at 65%. A resolution of 30,000 was used to collect full scan FTMS (Fourier Transform Mass Spectrometry) spectra with mass range between m/z 100 and 300. For all MS fragmentation experiments, a resolution of 15,000 was used along with activation Q of 0.250 and activation time of 10.0 ms. The normalized collision energy for $MS^2$ experiment of the parent ion was 31.0 eV with an isolation width of 1.0 m/z and scan range between m/z 60 and 240. For the $MS^3$ experiment of m/z 229.1547/142.0860, normalized collision energy was 31.0 and 25.0 eV for first and second stage fragmentation, respectively, with isolation width of m/z 2.0 for both stages and scan range between m/z 50 and 240. For the $MS^3$ experiment of m/z 229.1547/170.0810, normalized collision energy was 31.0 and 30.0 eV for first and second stage fragmentation, respectively. The isolation width was m/z 3.0 and 2.0 for first and second stage fragmentation, respectively, and scan range between m/z 50 and 240. For the $MS^4$ experiment of m/z 229.1547/142.0860/114.0911, normalized collision energy was 31.0, 20.0, and 20.0 eV for first to third stage fragmentation. Isolation width was m/z 2.0 for all the three stages and scan range between m/z 50 to 240.

What is claimed is:
1. A compound represented by the following formula:

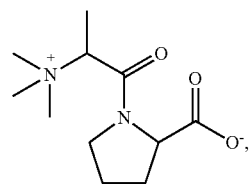

or a salt thereof, wherein the compound is at least 60%, 70%, 80%, 90%, 95%, 99%, 99.5% or 99.9% pure.

2. The compound of claim 1, wherein the compound is represented by the following formula:

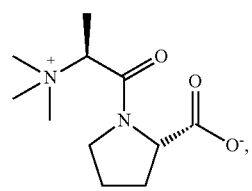

or a salt thereof.

3. The compound of claim 1, wherein the compound is isotopically labeled.

4. A method of determining the level of a compound represented by the following formula:

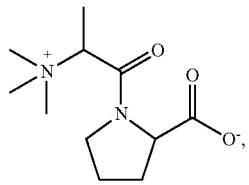

or a salt thereof, in a subject comprising:
(1) preparing an analytical sample from a biological sample obtained from the subject;
(2) determining the level of the compound using chromatography, mass spectrometry, enzyme-linked immunosorbent assay (ELISA), antibody linkage, immunoblotting, immunohistochemistry (IHC), other immunochemical methods, or a combination thereof.

5. The method of claim 4, further comprising comparing the level of the compound in the biological sample obtained from the subject to the level of the compound in a reference sample.

6. The method of claim 4, wherein the method further comprises using the determined level of the compound in a mathematical model to assess kidney function.

7. The method of claim 4, wherein the method further comprises analyzing the biological sample to determine the level of one or more additional biomarkers relevant for the assessment of kidney function.

8. The method of claim 7, wherein the additional biomarkers are selected from the group consisting of pseudouridine, N-acetylthreonine, 2-C-mannopyranosyl tryptophan, N-acetylserine, N-acetylalanine, N6-carbamoylthreonyl adenosine, 4-acetamidobutanoate, erythritol, myo-inositol, erythronate, urea, arabitol, N2,N2-dimethylguanosine, N1-methyladenosine, 3-methylglutarylcarnitine, S-adenosylhomocysteine, N-acetylmethionine, N6-acetyllysine, Kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate and p-cresol sulfate.

9. A The method of claim 4 further comprising calculating the estimated glomerular filtration rate (eGFR) of the subject using an algorithm that utilizes the determined level of the compound.

10. The method of claim 9, wherein the calculated estimated glomerular filtration rate (eGFR) is used for assessing kidney function in the subject.

11. The method of claim 4, wherein the compound is represented by the following formula:

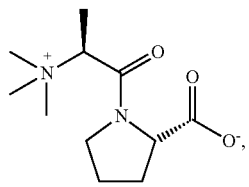

or a salt thereof.

12. A kit comprising a compound represented by the following formula:

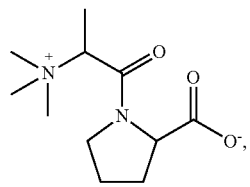

or a salt thereof, and instructions for measuring the level of the compound in a biological sample.

13. The kit of claim 12 further comprising
one or more instructions selected from the group consisting of assessing or monitoring kidney function in a subject,
determining predisposition to developing reduced kidney function in a subject,
classifying a subject according to level of kidney function,
diagnosing or monitoring chronic kidney disease (CKD) in a subject,
diagnosing or monitoring acute kidney injury (AKI) in a subject, and
calculating estimated glomerular filtration rate (eGFR) in a subject based on the level of the compound detected in a biological sample obtained from the subject.

14. The kit of claim 12, wherein the compound is represented by the following formula:

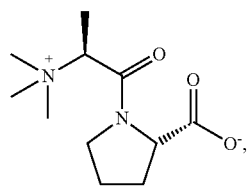

or a salt thereof.

15. The kit of claim 12, wherein the compound is isotopically labeled.

16. The kit of claim 15, wherein the compound is N,N,N-Trimethyl-$^{13}C_3$-L-Alanyl-L-Proline.

17. The kit of claim 12, wherein the kit further comprises one or more additional biomarkers selected from the group consisting of pseudouridine, N-acetylthreonine, 2-C-mannopyranosyl tryptophan, N-acetylserine, N-acetylalanine, N6-carbamoylthreonyl adenosine, 4-acetamidobutanoate, erythritol, myo-inositol, erythronate, urea, arabitol, N2,N2-dimethylguanosine, N1-methyladenosine, 3-methylglutarylcarnitine, S-adenosylhomocysteine, N-acetylmethionine, N6-acetyllysine, kynurenine, arabonate, succinylcarnitine, ribose, xylonate, N-formylmethionine, O-methylcatechol sulfate, 2-methylbutyrylcarnitine, phenylacetylglutamine, N2,N5-diacetylornithine, tryptophan, creatinine, urate, 3-indoxylsulfate and p-cresol sulfate.

18. A method for preparing a compound represented by the following formula:

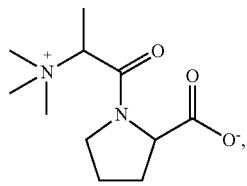

or a salt thereof, comprising reacting a compound represented by the following formula:

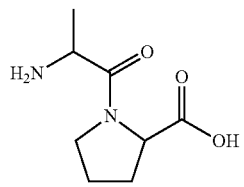

or a salt thereof, with a methylation reagent CH$_3$X or (CH$_3$)$_2$SO$_4$, wherein X is Cl, Br, I or OSO$_2$CF$_3$.

19. The method of claim 18, wherein the compound is represented by the following formula:

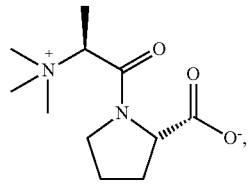

or a salt thereof, and the method comprises reacting L-alanyl-L-proline with CH$_3$X or (CH$_3$)$_2$SO$_4$.

* * * * *